United States Patent
DeFrees et al.

(10) Patent No.: US 7,842,677 B2
(45) Date of Patent: *Nov. 30, 2010

(54) SYNTHETIC GANGLIOSIDE DERIVATIVES AND COMPOSITIONS THEREOF

(75) Inventors: Shawn DeFrees, North Wales, PA (US); Zhi Guang Wang, Dresher, PA (US)

(73) Assignee: Seneb Biosciences, Inc., North Wales, PA (US)

( * ) Notice: Subject to any disclaimer, the term of this patent is extended or adjusted under 35 U.S.C. 154(b) by 1460 days.

This patent is subject to a terminal disclaimer.

(21) Appl. No.: 10/487,841

(22) PCT Filed: Aug. 29, 2002

(86) PCT No.: PCT/US02/27935

§ 371 (c)(1),
(2), (4) Date: Oct. 1, 2004

(87) PCT Pub. No.: WO03/017949

PCT Pub. Date: Mar. 6, 2003

(65) Prior Publication Data

US 2005/0239741 A1 Oct. 27, 2005

Related U.S. Application Data

(60) Provisional application No. 60/315,831, filed on Aug. 29, 2001.

(51) Int. Cl.
*A61K 31/739* (2006.01)
*C07H 17/02* (2006.01)

(52) U.S. Cl. .............................. 514/54; 514/53; 514/61; 536/17.4

(58) Field of Classification Search ................... 514/53, 514/54, 61; 536/17.4; 435/85
See application file for complete search history.

(56) References Cited

U.S. PATENT DOCUMENTS 3,954,881 A 5/1976 Bowler (Continued)

FOREIGN PATENT DOCUMENTS

| DE | 197 09 787 A1 | 9/1998 |
|---|---|---|
| EP | 0 119 539 A2 | 9/1984 |
| JP | 09 208461 A | 8/1997 |
| WO | WO 98/40390 A2 | 9/1998 |
| WO | WO 99/28491 A1 | 6/1999 |

OTHER PUBLICATIONS

Helling et al., Cancer Research, 1994, 54, 197-203.*
Jennemann, Richard et al., "Specific Immunization Using Keyhole Umpet Hemocyanin-Ganglioside Conjugates"; *Journal of Biochemistry*, 1994, vol. 115, No. 6, pp. 1047-1052.

Helling, Friedhelm et al., "$G_{D3}$ Vaccines for Melanoma: Superior Immunogenicity of Keyhole Limpet Hemocyanin Conjugate Vaccines"; *Cancer Research* 1994 vol. 54, pp. 197-203.
Ito, Yukishige et al., "A Novel Strategy for Synthesis of Ganglioside GM# Using an Enzymatically Produced Sialoside Glycosyl Donor"; *Journal of the American Chemical Society* 1983, vol. 115 No. 4, pp. 1603-1605.

(Continued)

*Primary Examiner* — Shaojia Anna Jiang
*Assistant Examiner* — Ganapathy Krishnan
(74) *Attorney, Agent, or Firm* — Morgan, Lewis & Bockius, LLP

(57) ABSTRACT

Novel synthetic gangliosides and pharmaceutical compositions containing such synthetic gangliosides are described. Methods of making the novel synthetic ganglioside compounds and compositions as well as their use in the field of neuroprotection and cancer treatment is also described.

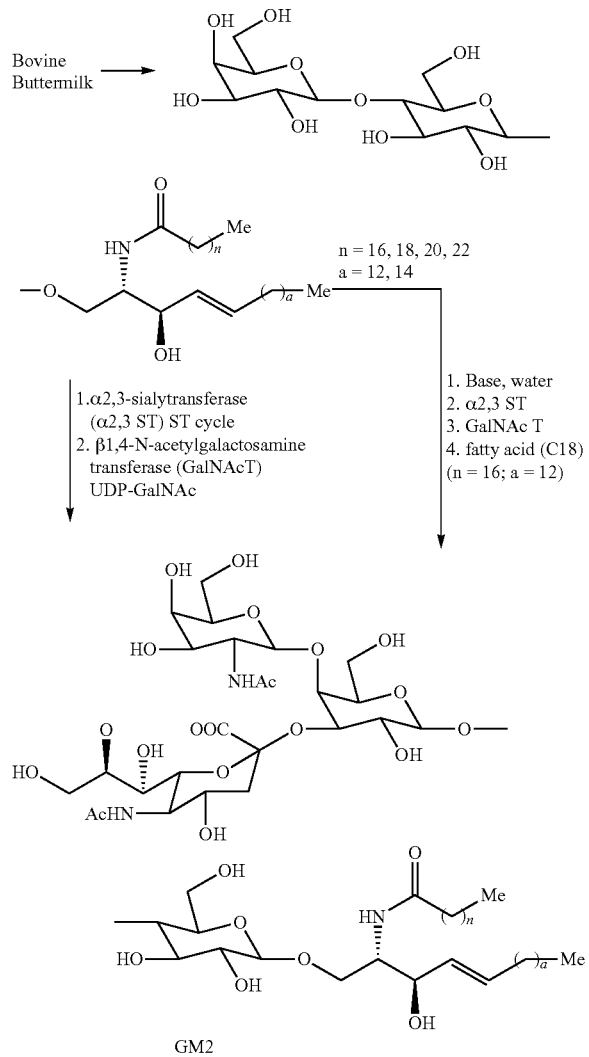

9 Claims, 15 Drawing Sheets

U.S. PATENT DOCUMENTS

| | | | | |
|---|---|---|---|---|
| 4,940,694 | A * | 7/1990 | della Valle et al. | 514/25 |
| 5,264,424 | A * | 11/1993 | Della Valle et al. | 514/54 |
| 7,273,852 | B2 * | 9/2007 | Tsuji et al. | 514/23 |
| 2005/0032742 | A1 | 2/2005 | DeFrees et al. | |
| 2005/0245735 | A1 | 11/2005 | DeFrees | |

OTHER PUBLICATIONS

Bertozzi, C.R., et al., "Carbon-Linked Galactosphingolipid Analogs Bind specifically to HIV-1 gp120," *J. Am. Cchem. Soc.*, 1992, vol. 114, No. 26, pp. 10639-10641.

Binder, W.H., et al., "Galactosylation by Use of B-Galactosidase Chemo-Enzymatic Syntheses of Di and Trisaccharides," *Tetrahedron*, 1994, vol. 50, No. 35, pp. 10407-10418.

De Rosa, S., et al., "Aliphatic and Aromatic Glycosides from the Cell Cultures of Lycopersicon Esculentum," *Phytochemistry*, 1998, vol. 42, No. 4, pp. 1031-1034.

Guivisdalsky, P.N., et al., Synthesis and Antineoplastic Properties of Ether-Linked Thioglycolipids, *J. Med. Chem.*, 1990, vol. 33, No. 9, pp. 2614-2621.

Koike, K., et al., "Total Synthesis of Cerebroside: (2S, 3R, 4E)-1-0-B-D-Galactopyranosyl-N(2'R and 2'S)-2'-Hydroxytetracosanoylsphingenine," *Carbohydrate Research*, 1987, vol. 162, pp. 237-246.

Marinier A., et al., "Sulfated Galactocerebrosides as Potential Antiinflammatory Agents," *J. Med. Chem.*, 1997, vol. 40, No. 20, pp. 3234-3247.

Pfäffli, P.J., et al., "Thioglycosides Having 0-Benzyl Blocking Groups as Intermediates for the Systematic, Sequential Synthesis of Oligosaccharides. Synthesis of isomaltose," *Carbohydrate Research*, 1972, vol. 23, pp. 195-206.

Sogin, David C., et al. "Binding of Cytochalasin B to human Erythrocyte Glucose Transporter," *Biochemistry*, 1980, vol. 19, No. 23, pp. 5417-5420.

Tsujihara, K., "A new class of Nitroureas. II synthesis and Antitumor Activity of 1-(2Chloroethyl)-3,3,Disubstituted-1nitrsoureas having a Glucopyranosyl, Mannopyranosyl or Galactopyranosyl Moiety," *Chem. Pharm. Bull.*, 1981, vol. 29, No. 11, pp. 3262-3273.

Yoshikawa, K., et al., "Aroma Glycosides from Hovenia Dulsis," *Phytochemistry*, 1993, vol. 34 No. 5, pp. 1431-1433.

* cited by examiner

SYNTHETIC GANGLIOSIDE DERIVATIVES AND COMPOSITIONS THEREOF

CROSS REFERENCE TO RELATED APPLICATIONS

This application claims benefit of priority under 35 U.S.C §119(e) to U.S. Provisional Application No. 60/315,831 filed on Aug. 29, 2001 which is herein incorporated in its entirety by reference.

BACKGROUND OF THE INVENTION

The term "carbohydrate" or "saccharide" embraces a wide variety of chemical compounds having the general formula $(CH_2O)_n$, such as monosaccharides, disaccharides, oligosaccharides and polysaccharides. Oligosaccharides and polysaccharides are chains composed of monosaccharide units, which are also generally referred to as sugars. The monosaccharide units of an oligo- or polysaccharide can be arranged in various orders. The linkage between any two saccharide units can occur in any of approximately ten different ways. As a result, the number of different possible stereoisomeric oligosaccharide or polysaccharide chains is enormous. Saccharides are a key component of glycosphingolipids found in cell membranes. Of interest with respect to the present invention is a certain class of glycoshingolipids known as gangliosides.

Gangliosides are glycosphingolipids, often found in cell membranes, that consist of three elements. One or more sialic acid residues are attached to an oligosaccharide or carbohydrate core moiety, which in turn is attached to a hydrophobic lipid (ceramide) structure which generally is embedded in the cell membrane. The ceramide moiety includes a long chain base (LCB) portion and a fatty acid (FA) portion. Gangliosides, as well as other glycolipids and their structures in general, are discussed in, for example, Lehninger, Biochemistry (Worth Publishers, 1981) pp. 287-295 and Devlin, Textbook of Biochemistry (Wiley-Liss, 1992). Gangliosides are classified according to the number of monosaccharides in the carbohydrate moiety, as well as the number and location of sialic acid groups present in the carbohydrate moiety. Mono sialogangliosides are given the designation "GM", disialogangliosides are designated "GD", trisialogangliosides "GT", and tetrasialogangliosides are designated "GQ". Gangliosides can be classified further depending on the position or positions of the sialic acid residue or residues bound. Further classification is based on the number of saccharides present in the oligosaccharide core, with the subscript "1" designating a ganglioside that has four saccharide residues (Gal-GalNAc-Gal-Glc-Ceramide), and the subscripts "2", "3" and "4" representing trisaccharide (GalNAc-Gal-Glc-Ceramide), disaccharide (Gal-Glc-Ceramide) and monosaccharide (Gal-Ceramide) gangliosides, respectively.

Numerous types of gangliosides found in nature have been isolated and identified and vary primarily in the basic saccharide structure (e.g. $G_{M3}$, $G_{M2}$, $G_{M1}$, $G_{D1a}$, $G_{D1b}$ and $G_{T1}$). A variety of procedures are available for the isolation and purification of such "natural" gangliosides from organs and tissues, particularly from animal brain (Sonnino et al., 1992, J. Lipid Res., 33:1221-1226; Sonnino et al., 1988, Ind. J. Biochem. Biophys., 25:144-149; Svennerholm, 1980, Adv. Exp. Med. Biol., 125:533-44) as well as bovine buttermilk (Ren et al., 1992, J. Bio. Chem., 267:12632-12638; Takamizawa et al., 1986, J. Bio. Chem., 261:5625-5630).

Gangliosides are normal components of plasma membranes and are particularly abundant in the nervous system. In humans, gangliosides are most abundant in the gray matter of the brain, particularly in nerve endings. They are believed to be present at receptor sites for neurotransmitters, including acetylcholine, and can also act as specific receptors for other biological macromolecules, including interferon, hormones, viruses, bacterial toxins, and the like.

Certain gangliosides are found on the surface of human hematopoictic cells (Hildebrand et al. (1972) Biochim. Biophys. Acta 260: 272-278; Macher et al. (1981) J. Biol. Chem. 256: 1968-1974; Dacremont et al. Biochim. Biophys. Acta424: 315-322; Klock et al. (1981) Blood Cells 7:247) which may play a role in the terminal granulocytic differentiation of these cells. Nojiri et al. (1988) J Biol. Chem. 263: 7443-7446. These gangliosides, referred to as the "neolacto" series, have neutral core oligosaccharide structures having the formula [Galβ-(1,4)GlcNAcβ(1,3)]$_n$Galβ(1,4)Glc, where n=1-4. Included among these neolacto series gangliosides are 3'-nLM$_1$ (NeuAcα(2,3)Galβ(1,4)GlcNAcβ(1,3)Galβ(1,4)-Glcβ(1,1)-Ceramide) and 6'-nLM$_1$ (NeuAcα(2,6)Galβ(1,4)GlcNAcβ(1,3)Galβ(1,4)-Glc,(1,1)-Ceramide).

It has been widely demonstrated that gangliosides are able to enhance functional recovery both in the lesioned peripheral nervous system (PNS) and the central nervous system (CNS), through the involvement of specific membrane mechanisms and the interaction with trophic factors, as pointed out from studies in vitro on neuronal cultures (Ferrari, F. et al., Dev. Brain Res., 1983, 8:215-221; Doherty, P. et al., J. Neurochem., 1985, 44:1259-1265; Skaper, S. D. et al., Mol. Neurobiol., 1989, 3:173-199). Gangliosides have been used for treatment of nervous system disorders, including cerebral ischemic strokes. See, e.g., Mahadnik et al. (1988) Drug Development Res. 15: 337-360; U.S. Pat. Nos. 4,710,490 and 4,347,244; Horowitz (1988) Adv. Exp. Med. and Biol. 174: 593-600; Karpiatz et al. (1984) Adv. Exp. Med. and Biol. 174: 489-497.

As a result, attempts have been made to use gangliosides in the treatment of disorders of the nervous system. This has led to the development of synthetic gangliosides as well as natural ganglioside containing compositions for use in the treatment of disorders of the nervous system (U.S. Pat. Nos. 4,476,119, 4,593,091, 4,639,437, 4,707,469, 4,713,374, 4,716,223, 4,849,413, 4,940,694, 5,045,532, 5,135,921, 5,183,807, 5,190,925, 5,210,185, 5,218,094, 5,229,373, 5,260,464, 5,264,424, 5,350,841, 5,424,294, 5,484,775, 5,519,007, 5,521,164, 5,523,294, 5,677,285, 5,792,858, 5,795,869, and 5,849,717).

Gangliosides have also been implicated as playing a significant role in certain types of cancer. Neuroblastoma is a form of cancer that primarily afflicts children under the age of five. Individuals suffering from neuroblastoma may have tumors growing near the spinal cord, and very large tumors have been found to cause paralysis in such patients. Gangliosides have been shown to play a role in both the growth and the inhibition of the growth of neuroblastoma-associated tumors (Basavarajappa et al., 1997, Alcohol Clin. Exp. Res., 21(7):1199-203; Singleton et al., 2000, Int. J. Dev. Neurosci., 2000, 18(8):797-80).

However, there still exists a need in the art for compounds capable of acting as neuroprotective agents in a manner similar to or better than the natural gangliosides for the prophylaxis, treatment and cure of disorders of the nervous system. Further, differences in the structure of ganglioside compounds can refine the structure-function relationship of such compounds to provide powerful tools for control of the growth of certain kinds of tumors, including neuroblastoma tumors.

SUMMARY OF THE INVENTION

The present invention answers such a need by providing novel synthetic gangliosides of formulae (I) and (Va)-(Vd):

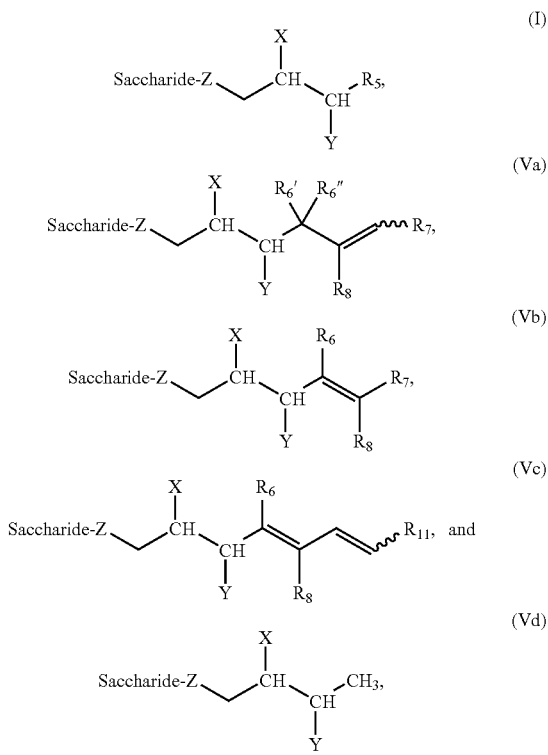

including pharmaceutically acceptable salts, isomers, hydrates, solvates, and prodrugs thereof.

The invention further provides a novel synthetic ganglioside of the formula

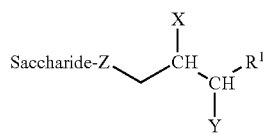

in which Z can be O, S, $C(R^2)_2$ and $NR^2$, X can be H, $-OR^3$, $-NR^3R^4$, $-SR^3$, and $-CHR^3R^4$, and $R^1$, $R^2$ and $R^3$ can be independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, $-C(=M)R^5$, $-C(=M)-Z-R^5$, $-SO_2R^5$, and $-SO_2$ functional moieties. Further, a novel ganglioside of the present invention can have M and Z independently selected from O, $NR^6$ or S, and Y can be selected from H, $-OR^7$, $-SR^7$, $-NR^7R^8$, substituted or unsubstituted alkyl, substituted or unsubstituted heteroalkyl, substituted or unsubstituted aryl, substituted or unsubstituted heteroaryl, and substituted or unsubstituted heterocycloalkyl moieties. Further still a novel ganglioside of the invention can have $R^5$, $R^6$, $R^7$ and $R^8$ independently selected from H, substituted or unsubstituted alkyl, substituted or unsubstituted heteroalkyl, substituted or unsubstituted aryl, substituted or unsubstituted heterocycloalkyl moieties.

The present invention also provides a novel ganglioside compound as described above, with the proviso that when X is $NHR^4$, in which $R^4$ is selected from H and $-C(=O)R^5$, in which $R^5$ is substituted or unsubstituted alkyl, Y is OH; and Z is O, $R^5$ is other than a substituted or unsubstituted alkyl moiety.

The present invention also provides a novel ganglioside compound in which the saccharide component can be

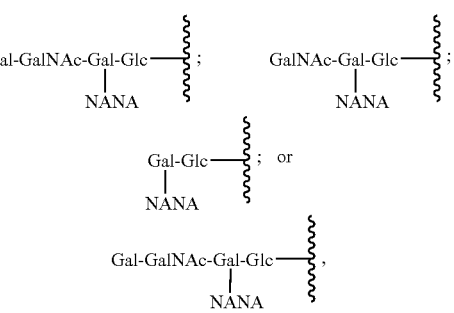

and such saccharide moieties may or may not be deacetylated.

The invention further provides pharmaceutical compositions including at least one compound of the invention and a pharmaceutically acceptable carrier.

The invention still further provides a method for the prevention and/or treatment and/or cure of a disorder of the nervous system in an animal or human including the step of administering to a patient in need thereof a therapeutically effective amount of at least one compound or pharmaceutical composition of the invention. Such patients in need of a compound of the present invention may suffer from a disorder of the nervous system, including Parkinson's disease, ischemia, stroke, Alzheimer's disease, depression, anxiety, encephalitis, meningitis, amyotrophic lateral sclerosis, trauma, spinal cord injury, nerve injury, and nerve regeneration.

One embodiment of the invention provides a method for the treatment of a glioma in a human and includes the step of administering to the human in need thereof a therapeutically effective amount of a compound of the present invention.

The present invention also provides a method of synthesizing a synthetic ganglioside compound of the invention, wherein the steps of synthesis of the saccharide moiety include contacting a sphingoid acceptor molecule and a glucose molecule with a galactosyltransferase enzyme and a galactose donor molecule to form

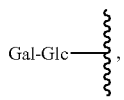

contacting the

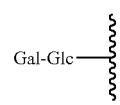

with a trans-sialidase enzyme and a sialic acid (NANA) donor molecule to form

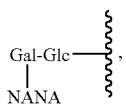

contacting the

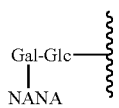

with a N-acetyl galactose (GalNAc)-transferase enzyme and a GalNAc donor molecule to form

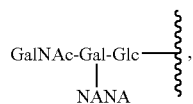

contacting the

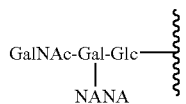

with a galactosyltransferase enzyme and a galactose (Gal) donor molecule to form

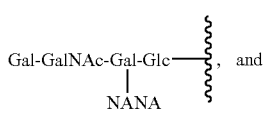

contacting the

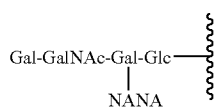

with a fatty acid moiety under conditions sufficient to form a ganglioside.

BRIEF DESCRIPTION OF THE DRAWINGS

FIG. 6 shows that compound 1003, at 50 AIM, causes almost 100% growth inhibition in all cell lines (86-100%).

FIG. 7 shows that compound 1009 has a profile similar to that for compound 1003 in four cell lines (77-89% growth inhibition with 50 μM compound 1009) and in U-118 cells, the growth inhibition with 50 μM compound 1009 is 21%.

FIG. 8 shows that compound 1011 has activity similar to compound 1003, with the exception that the inhibition of 9L cells by 50 μM compound 1011 was 46%.

FIG. 9 shows that compound 1014, when used to treat Hs 683 and Sw1088 cells, inhibited proliferation 42% and 35%, respectively, when used at a concentration of 50 μM.

FIG. 10 shows that 50 μM compound 1081 inhibited proliferation of 9L 23%, U-118 cells 27%, Hs 683 cells 48%, and Sw 1088 cells 68%.

FIG. 11 shows that compound 1082 inhibited the growth of 9L cells 11-37%.

FIG. 12 shows that compound 1083, at 5 μM, inhibited growth of 9L and Hs 683 cells (27% and 32%, respectively). At 50 μM, compound 1083 inhibited growth of 9L, Hs 683, U-118, and Sw 1088 cells 26-54%.

FIG. 13 shows that compound 1084 strongly inhibited growth in all cell lines at 50 μM compound (91-100%).

FIG. 14 shows that compound 1085 was very active in the cell proliferation assay. Compound 1085 demonstrated growth inhibition activity at 5 μM in all cell lines tested (15-88%), and strong growth inhibition at 50 μM in all cell lines (95-100%).

FIG. 15 shows that compound 1086, at 50 μM, inhibits growth of all cell lines 66-100%.

DEFINITIONS

Figure 1:
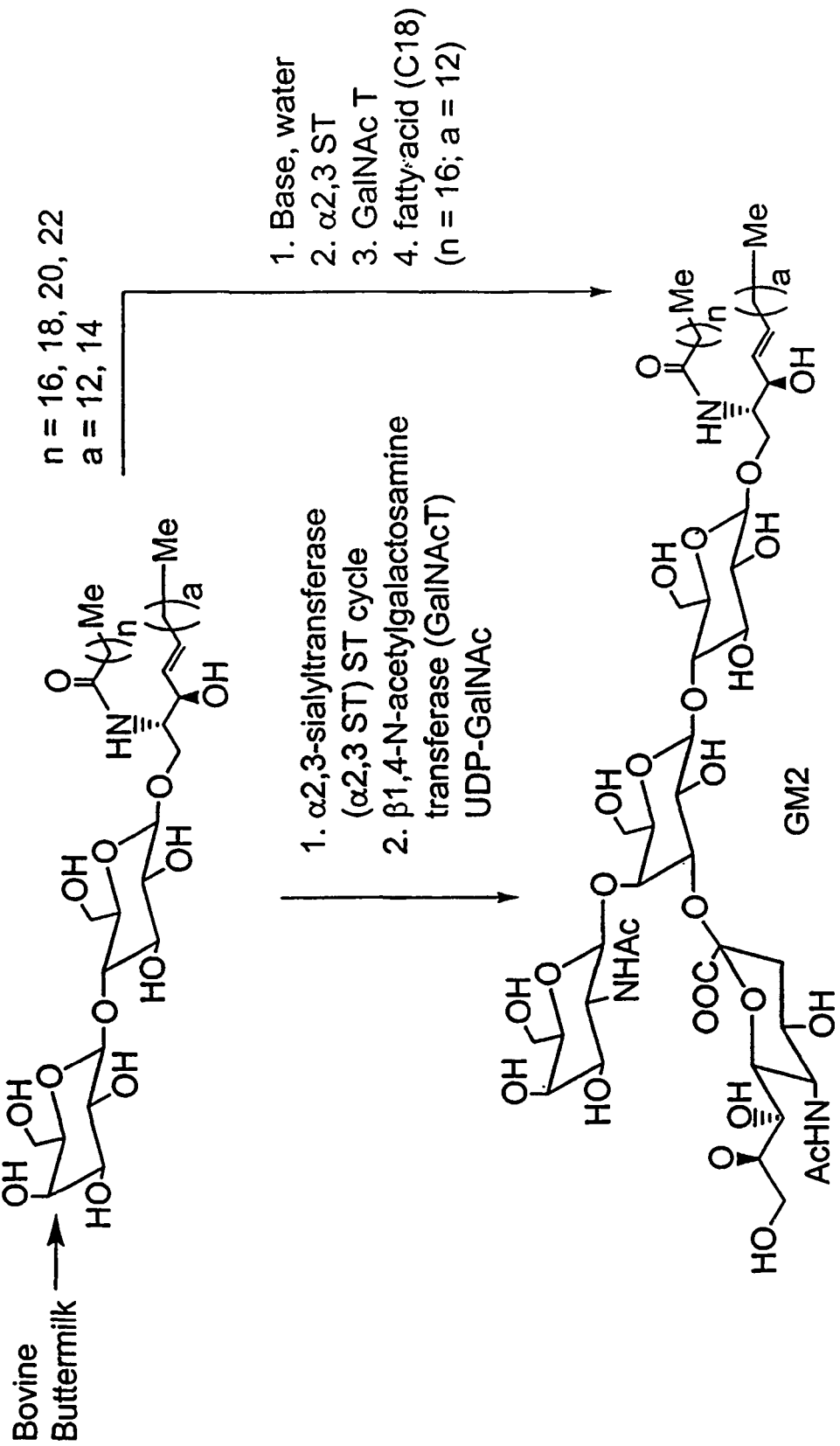
FIG. 1 shows a schematic diagram of two methods for synthesis of the ganglioside GM2 by enzymatic synthesis using as the starting material lactosylceramide obtained from bovine buttermilk.

In accordance with the invention and as used herein, the following terms are defined with the following meanings, unless explicitly stated otherwise.

The article "a" and "an" as used herein refers to one or to more than one (i.e. at least one) of the grammatical object of the article. By way of example, "an element" means one element or more than one element.

The term "alkenyl" as used herein refers to a substituted or unsubstituted trivalent straight chain or branched chain unsaturated aliphatic radical that includes at least two carbons joined by a double bond.

The term "alkynyl" as used herein refers to a straight or branched chain aliphatic radical that includes at least two carbons joined by a triple bond. If no number of carbons is specified, "alkenyl" and "alkynyl" each refer to radicals having from 2-12 carbon atoms.

The term "cycloalkyl" as used herein refers to a substituted or unsubstituted saturated aliphatic ring system, preferably a mono-, bi-, or tricyclic saturated aliphatic ring system. Examples include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), and [2.2.2]bicyclooctane The term "aromatic" is intended to mean stable substituted or unsubstituted mono-, bi-, tri-, polycyclic ring structures having only carbon atoms as ring atoms including, but not limited to, a stable monocyclic ring which is aromatic having six ring atoms; a stable bicyclic ring structure having a total of from 7 to 12 carbon atoms in the two rings of which at least one of the rings is aromatic; and a stable tricyclic ring structure having a total of from 10 to 16 atoms in the three rings wherein the tricyclic ring structure of which at least one of the ring is aromatic. Any non-aromatic rings present in the monocyclic, bicyclic, tricyclic or polycyclic ring structure may independently be saturated, partially saturated or fully saturated. Examples of such "aromatic" groups include, but are not limited to, phenyl and naphthyl.

The term "arylalkyl" as used herein refers to one, two, or three substituted or unsubstituted aryl groups having the number of carbon atoms designated appended to an alkyl group having the number of carbon atoms designated. The direction of attachment of an arylalkyl group to the remainder of the molecule may be through either the aryl or alkyl portion of the group. Suitable arylalkyl groups include, but are not limited to, benzyl, picolyl, naphthylmethyl, phenethyl, benzylhydryl, trityl, and the like, all of which may be optionally substituted.

As used herein the term "heteroaryl," "heteroaromatic" or "aromatic heterocyclic ring system" refers to a monocyclic, bicyclic or polycyclic, substituted or unsubstituted heterocyclic ring system containing at least one aromatic ring.

The term "substituted" as used herein means that a hydrogen atom has been replaced with another monovalent group (e.g. halo, haloalkyl, hydroxy, thiol, alkoxy, thiohaloalkyl, amino, and the like).

The terms "halo" or "halogen" as used herein refer to Cl, Br, F or I. The term "haloalkyl" and the like, refer to an alkyl group, as defined herein, wherein at least one hydrogen atom of the alkyl group is replaced by a Cl, Br, F or I. A mixture of different halo atoms may be used if more than one hydrogen atom is replaced. For example, a haloalkyl includes chloromethyl (—$CH_2$Cl) and trifluoromethyl (—$CF_3$) and the like.

The term "methylene" refers to —$CH_2$—.

Where substituent groups are specified by their conventional chemical formulae, written from left to right, they equally encompass the chemically identical substituents which would result from writing the structure from right to left, e.g., —$CH_2$O— is intended to also recite —O$CH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the allyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Examples of "heterocycles", "heterocyclic rings" or "heterocyclic ring systems" include, but are not limited to, acridinyl, azocinyl, benzimidazolyl, benzofuranyl benzothiofuranyl benzothiophenyl, benzoxazolyl, benzthiazolyl, benztriazolyl, benztetrazolyl, benzisoxazolyl, benzisothiazolyl, benzimidazalinyl, carbazolyl, 4aH carbazolyl, carbolinyl, chromanyl chromenyl cinnolinyl, decahydroquinolinyl 2H,6H-1,5,2-dithiazinyl, dihydrofuro[2,3-b]tetrahydrofuran furanyl, furazanyl, imidazolidinyl, imidazolinyl, imidazolyl, 1H-indazolyl, indolinyl, indolizinyl, indolyl 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2, 5-oxadiazolyl, 1,3,4-oxadiazolyl, oxazolidinyl, oxazolyl, oxazolidinyl pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl pyrazolinyl, pyrazolyl, pyridazinyl pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Also included are fused ring and spiro compounds containing, for example, the above heterocyclic ring structures.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl 1-naphthyl, 2-naphthyl, 4-biphenyl, 1-pyrrolyl, 2-pyrrolyl, 3-pyrrolyl 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl 5-thiazolyl, 2-furyl, 3-furyl 2-thienyl, 3-thienyl, 2-pyridyl, 3-pyridyl, 4-pyridyl 2-pyrimidyl, 4-pyirimdyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heterocycloalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR$SO_2$R', —CN and —$NO_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR$SO_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula —T—C(O)—CRR')$_q$—U—, wherein T and U are independently —NR—, —O—, CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Pharmaceutically acceptable acid addition salt" as used herein refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" as used herein refers to those salts derived from inorganic bases such as sodium, potassium, lithium, ammonium, calcium, magnesium, iron, zinc, copper, manganese, aluminum salts and the like. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like.

The term "biological property" as used herein means an in vivo activity that is directly or indirectly performed by a compound or pharmaceutical composition of the invention that is often shown by in vitro assays. In the present invention, the biological property is neuroprotection, including the prophylaxis, treatment and/or cure of disorders of the nervous system.

The term "isomer" as used herein refers to a compound having the same number and kind of atoms and hence the same molecular weight as another compound, but differing in respect to the arrangement or configuration of the atoms of the compound (e.g. cis and trans isomers). The term "isomer" also includes stereoisomers, diastereoisomers, enantiomers or mixtures thereof The D-isomer is preferred.

The term "substructure" as used herein refers to a portion of a chemcial compound. For example, a single aromatic ring of a napthalene structure is herein referred to as a substructure of the entire napthalene molecule.

The term "hydrate" as used herein refers to the product of water with a compound of the invention such that the H—OH bond is not split. A compound of the invention may form more than one hydrate. However, the amount of water in a hydrate of the invention is such that the compound remains stable. Preferably, a hydrate of a compound of the invention contains about 0.1-10% water.

The term "prodrug" as used herein refers to a pharmacologically inactive derivative or precursor of a compound of the invention which upon biotransformation, either spontaneous or enzymatic, within an organism releases a compound of the invention as a pharmaceutically active drug. A prodrug derivative of a compound of the invention contain groups cleavable under metabolic conditions such as, for example, solvolysis under physiological conditions or enzymatic degradation. According to the invention, a compound of the invention resulting from the biotransformation of its prodrug derivative are pharmaceutically active in vivo. Prodrug derivatives of a compound of the invention may be designated as single, double, triple, etc., corresponding to the number of biotransformation steps required to release the pharmaceutically active compound of the invention within the organism and/or indicating the number of functionalities present in the prodrug derivative. Prodrugs often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992).

As used herein, the term "saccharide" may be used interchangeably with the term "carbohydrate" and refers to single simple sugar moieties or monosaccharides as well as combinations of two or more single sugar moieties or monosaccharides covalently linked to form disaccharides, oligosaccharides, and polysaccharides. The term "saccharide" also includes N-acetylated and N-deacylated derivatives of such monosaccharides, disaccharides, oligosaccharides, and polysaccharides. Saccharides for use in the invention may be linear or branched. Examples of suitable monosaccharides include, but are not limited to, known aldoses and ketoses (i.e. aldehyde and ketone derivatives of straight-chain polyhydroxy alcohols containing at least three carbon atoms) including, for example, glyceraldehyde, erythrose, threose, ribose (Rib), arabinose (Ara), xylose (Xyl), lyxose (Lyx), allose, altrose, glucose (Glc), mannose (Man), gulose, idose, galactose (Gal), talose, dihydroxyacetone, erythrulose, ribulose, xylulose, psicose, fructose (Frc), sorbose, and tagatose. Other examples of suitable monosaccharides include, but are not limited to, fucose (Fuc), N-acetylneuraminic acid (also called sialic acid, NANA, or NAN (Sia)), N-acetylglucosamine (GlcNAc), and N-acetylgalactosamine (GalNAc). The cyclic hemiacetal and hemiketal forms of the monosaccharides are contemplated within the defined term. Other examples of suitable saccharides include, but are not limited to, those illustrated in FIG. 1.

As used herein, the term "disaccharide" refers to a saccharide composed of two monosaccharides linked together by a glycosidic bond. Examples of disaccharides include, but are not limited to, lactose (Lac) (glycosidic bond between Gal and Glc), sucrose (Suc) (glycosidic bond between Frc and Glc), and maltose (Mal), isomaltose and cellobiose (glycosidic bond between Glc and Glc).

The term "oligosaccharide" includes an oligosaccharide that has a reducing end and a non-reducing end, whether or not the saccharide at the reducing end is in fact a reducing sugar. In accordance with accepted nomenclature, an oligosaccharide is depicted herein with the non-reducing end on the left and the reducing end on the right. An oligosaccharide described herein may be described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3,2→3, 2-3, or (2,3).

The term "sphingoid," as used herein, includes sphingosines, phytosphingosines, sphinganines, ceramides, and the like. Both naturally occurring and synthetically produced compounds are included.

The term "glycosphingolipid" is a carbohydrate-containing derivative of a sphingoid or ceramide. The carbohydrate residue is attached by a glycosidic linkage to O-1 of the sphingoid.

The term "sialic acid" (abbreviated "Sia") refers to any member of a family of nine carbon carboxylated sugars. The most common member of the sialic acid family is N-acetyl-neuraminic acid (2-keto-5-acetamindo-3,5-dideoxy-D-glyc-ero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al. (1990) J. Biol. Chem. 265: 21811-21819. Also included are 9-substituted sialic acids such as a 9-O—$C_1$-$C_6$ acyl-Neu5Ac like 9-O-lactyl-Neu5Ac or 9-O-acetylNeu5Ac, 9-deoxy-9-fluoro-Neu5Ac and 9-azido-9-deoxy-Neu5Ac. For review of the sialic acid family, see, e.g., Varki (1992) Glycobiology 2:25-40; Sialic Acids: Chemistry, Metabolism and Function, R. Schauer, Ed. (Springer-Verlag, New York (1992). The synthesis and use of sialic acid compounds in a sialylation procedure is described in, for example, international application WO 92/16640, published Oct. 1, 1992.

As used herein, the term "linker" refers to any element, atom, molecule, that serves to join one portion of a molecule to another. Linkers are well known to those skilled in the art. Linkers can be mono- or multifunctional.

As used herein, the term "donor" refers to any molecule that serves to donate or provide a monosaccharide for addition to a growing saccharide chain or acceptor molecule. Thus the sugar moiety serves as one part of a donor molecule. Generally, the monosaccharide moiety is transferred from the donor to an "acceptor," as defined herein, by means of an enzymatic reaction. Donor molecules include those known to those of skill in the art and will vary depending upon the desired monosaccharide to be transferred.

As used herein, the term "contacting" or "contact" in relation to an enzyme and "donor" and an "acceptor" to form a growing saccharide chain means bringing the enzyme and donor into association with the "acceptor" or growing saccharide chain to affect the addition of a new monosaccharide unit to the acceptor or growing saccharide chain.

As used herein, the term "acceptor" refers to a molecule capable of receiving a monosaccharide moiety from a donor, each as defined herein. An "acceptor" may accept more than one monosaccharide such that a linear or branched "saccharide," as defined above, can be formed. Thus, the term "acceptor" includes a molecule containing a growing saccharide chain.

As used herein, the term "non-immobilized" in reference to an "acceptor", as defined herein, means that the acceptor is not affixed or bound to a substrate. For example, an acceptor that is in solution would be a "non-immobilized" acceptor.

The term "glycosyltransferase" as used herein refers to enzymes that catalyze the transfer of sugar moieties from activated donor molecules to specific acceptor molecules, each as defined herein, forming glycosidic bonds. Examples of glycosyltransferases include, but are not limited to, galactosyltransferase, glucosyltransferase, fucosyltransferase, and GalNActransferase. Further, glycosyltransferases may be classified according to the stereochemistries of the reaction substrates and products as either retaining, i.e., leading to retention of the anomeric configuration (for instance UDP-glucose→$\alpha$-glucoside), or inverting, i.e., leading to inversion of the anomeric configuration (for instance UDP-glucose→$\beta$-glucoside) (Sinnott, M. L. (1990) Chem. Rev. 90, 1171-1202). The classification groupings of families of glycosyltransferases is explained by Coutinho, P. M. & Henrissat, B. (1999) Carbohydrate-Active Enzymes server, which can be found on the Internet at <<afmb.cnrs-mrs.fr/~pedro/CAZY/db.html>>.

As used herein, the term "trans-sialidase" refers to an enzyme that catalyzes the addition of a sialic acid to galactose by means of an $\alpha$-2,3 glycosidic linkage. Trans-sialidases may be found in many Trypanosomy species and some other parasites. Trans-sialidases of these parasite organisms retain the hydrolytic activity of usual sialidase, but with much less efficiency, and catalyze a reversible transfer of terminal sialic acids from host sialoglycoconjugates to parasite surface glycoproteins in the absence of CMP-sialic acid. *Trypanosome cruzi*, which causes Chagas disease, has a surface trans-sialidase the catalyzes preferentially the transference of $\alpha$-2,3-linked sialic acid to acceptors containing terminal $\beta$-galactosyl residues, instead of the typical hydrolysis reaction of most sialidases (Ribeirão et al., 1997, Glycobiol., 7:1237-1246; Takahashi et al., 1995, Anal. Biochem., 230:333-342; Scudder et al., 1993, J. Biol. Chem., 268:9886-9891; Vandekerckhove et al., 1992, Glycobiol., 2:541-548). *T. cruzi* trans-sialidase (TcTs) has activity towards a wide range of saccharide, glycolipid, and glycoprotein acceptors which terminate with a $\beta$-linked galactose residue, and synthesizes exclusively an a2-3 sialosidic linkage (Scudder et al., supra). At a low rate, it also transfers sialic acid from synthetic $\alpha$-sialosides, such as p-nitrophenyl-$\alpha$-N-acetylneuraminic acid, but NeuAc2-3Gal$\beta$1-4(Fuc$\alpha$1-3)Glc is not a donor-substrate. Modified 2-[4-methylumbelliferone]-$\alpha$-ketoside of N-acetyl-D-neuraminic acid (4MU-NANA) and several derivatives thereof can also serve as donors for TcTs (Lee & Lee, 1994, Anal. Biochem, 216:358-364). Enzymatic synthesis of 3'-sia-lyl-lacto-N-biose I has been catalyzed by TcTs from lacto-N-biose I as acceptor and 2'-(4-methylumbellyferyl)-$\alpha$-D-N-acetylneuraminic as donor of the N-acetylneuraminil moiety (Vetere et al., 2000, Eur. J. Biochem., 267:942-949). Further information regarding the use of trans-sialidase to synthesize α2,3-sialylated conjugates can be found in European Patent Application No. 0 557 580 A2 and U.S. Pat. No. 5,409,817. The intramolecular trans-sialidase from the leech *Macrobdella decora* exhibits strict specificity toward the cleavage of terminal Neu5Ac N-acetylneuraminic acid) α2→3Gal linkage in sialoglycoconjugates and catalyzes an intramolecular trans-sialosyl reaction (Luo et al., 1999, J. Mol. Biol., 285: 323-332). Trans-sialidases primarily add sialic acid onto galactose acceptors, but will transfer sialic acid onto some other sugars. Transfer of sialic acid onto GalNAc, however, requires a sialyltransferase. Further information on the use of trans-sialidases can be found in PCT Application No. WO 93/18787; Vetere et al., 1997, Eur. J. Biochem., 247:1083-1090.

As used herein, the term "sialyltransferase" refers to enzymes that catalyze glycoside synthesis by inversion of the configuration of the added sugar and which require sugar nucleotides as the monosaccharide donor. An example of a sialyltransferase is the enzyme from the trypanosome *Trypanosoma rangeli* called TrSA (Buschiazzo et al., 2000, EMBO J., 19:16-24).

DETAILED DESCRIPTION OF THE INVENTION

The invention provides a novel synthetic ganglioside of formula (I):

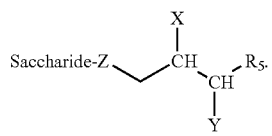

(I)

In formula (I):

the saccharide is as defined herein selected from the group consisting of a monosaccharide, a disaccharide, an oligosaccharide, a polysaccharide, an N-acetylated derivative thereof, and an N-deacylated derivative thereof;

Z is O, S, or —$NR_1$;
X is H, —$OR_1$, —$NR_1R_2$, —$SR_1$, or —$CHR_1R_2$;
$R_1$ and $R_2$ are independently H, —$CH_2R_3$, —$C(=M)R_3$, —$C(=M)$-p-$R_3$, —$SO_2R_3$, —$SO_3$, alkyl, cycloalkyl, aryl, arylalkyl, heteroaryl, heteroalkyl, or haloalkyl;
M is O, $NR_4$ or S;
$R_4$ is H, alkyl, cycloalkyl, aryl, arylalkyl, heteroaryl, heteroalkyl, or haloalkyl;
p is O, —$NR_4$, or S, where $R_4$ is as set forth above;
$R_3$ is H, alkyl, cycloalkyl, arylalkyl, haloalkyl, aryl, heteroaryl, or heteroalkyl;
Y is H, —$OR_1$, —$SR_1$, —$NR_1R_2$, branched alkyl, cycloalkyl, aryl, arylalkyl, heteroaryl, heteroalkyl, or haloalkyl, where $R_1$ and $R_2$ is as set forth above; and
$R_5$ is H, alkyl, cycloalkyl, alkenyl, aryl, arylalkyl, heteroaryl, heteroalkyl, or haloalkyl;
and all pharmaceutically acceptable salts, isomers, hydrates, prodrugs, and solvates thereof with the proviso that when Z is O, Y is OH, and $R_5$ is alkenyl, X is not any of —$NH_2$, —NH(alkyl), —NHC(=O)alkenyl, —NHC(=O) fluoroalkyl, and —NHC(=O)alkyl.

The invention also provides a novel synthetic ganglioside of formula (II):

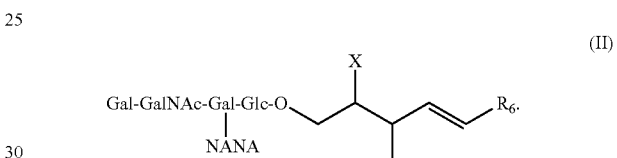

(II)

wherein:
X is —OH, —OC(=O)-$C_1$-$C_{11}$alkyl, or —OC(=O)-haloalkyl; and
$R_5$ is a $C_1$-$C_{18}$ alkyl; and
and all pharmaceutically acceptable salts, isomers, hydrates, prodrugs, and solvates thereof.

The invention further provides compounds of formula (II) as set forth in Table 1 below and include their pharmaceutically acceptable salts, isomers, hydrates, prodrugs, and solvates:

TABLE 1

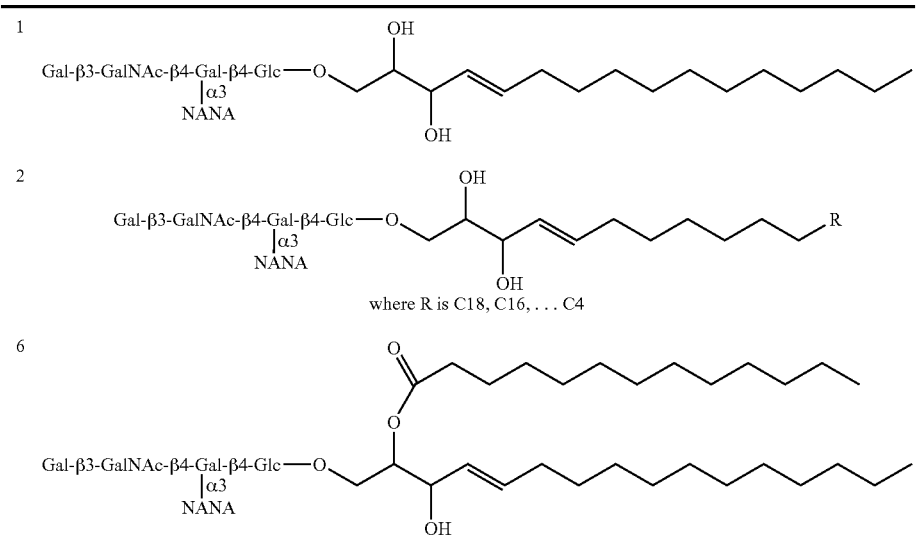

TABLE 1-continued

| 7 | 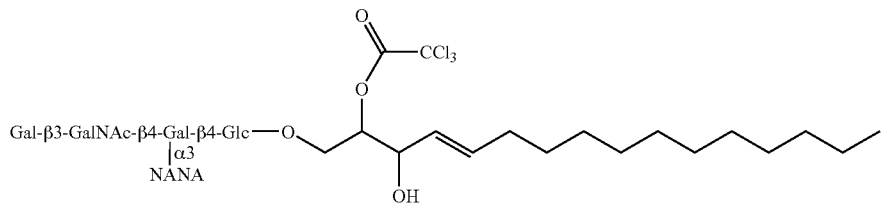 |
| --- | --- |
| 8 | 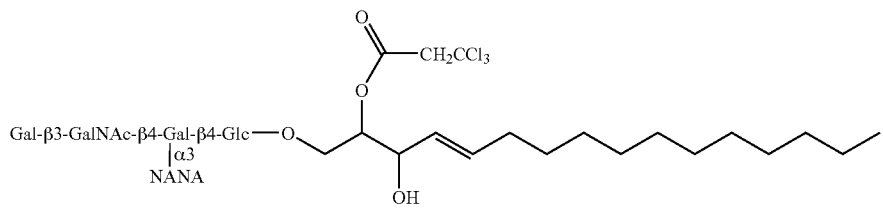 |
| 9 | 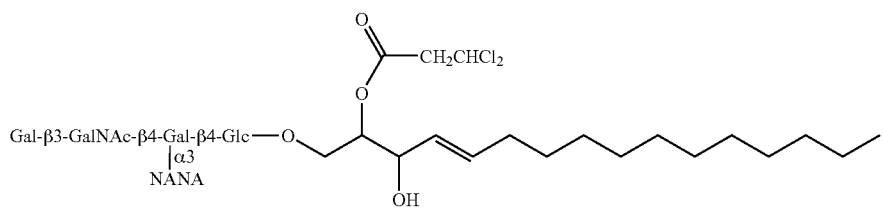 |
| 10 | 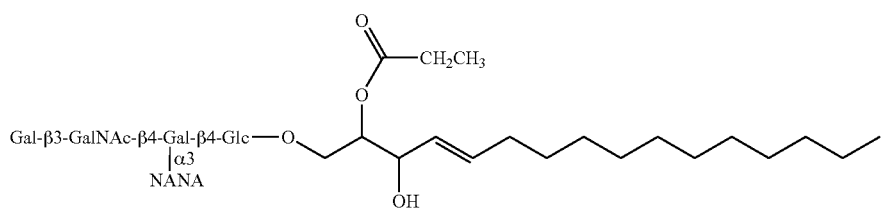 |
| 11 | 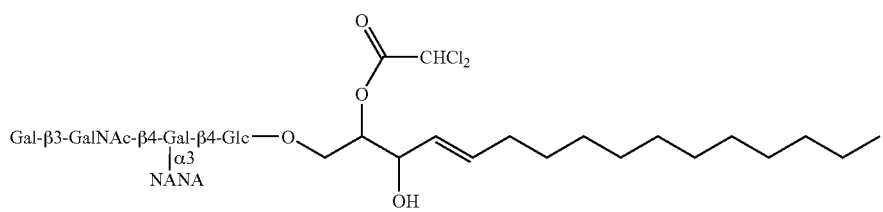 |
| 12 | 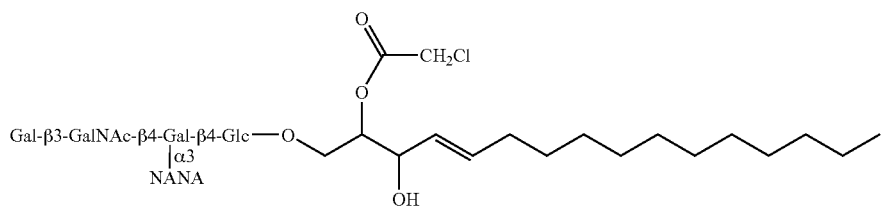 |

The invention also provides synthetic gangliosides of formula (III):

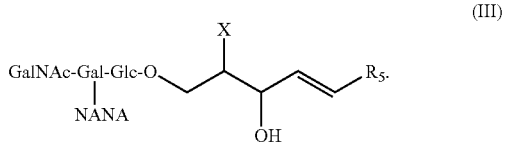

(III)

wherein:

X is —OH, —OC(=O)-$C_1$-$C_{11}$alkyl, or —OC(=O)-haloalkyl; and $R_5$ is a $C_1$-$C_{18}$ alkyl; and and all pharmaceutically acceptable salts, isomers, hydrates, prodrugs, and solvates thereof.

The invention further provides compounds of formula (III) as set forth in Table 2 below and include their pharmaceutically acceptable salts, isomers, hydrates, prodrugs, and solvates:

TABLE 2

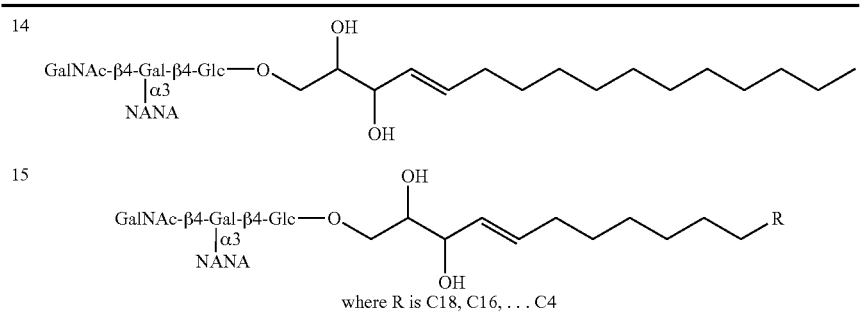

The invention also provides a synthetic ganglioside of formula (IV):

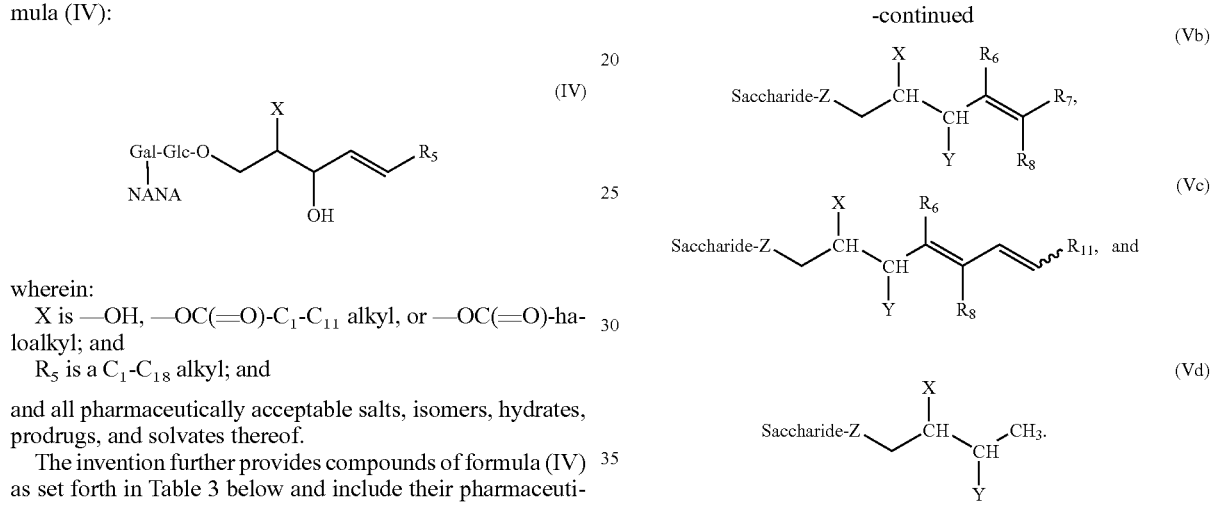

wherein:

X is —OH, —OC(=O)-$C_1$-$C_{11}$ alkyl, or —OC(=O)-haloalkyl; and $R_5$ is a $C_1$-$C_{18}$ alkyl; and and all pharmaceutically acceptable salts, isomers, hydrates, prodrugs, and solvates thereof.

The invention further provides compounds of formula (IV) as set forth in Table 3 below and include their pharmaceutically acceptable salts, isomers, hydrates, prodrugs, and solvates:

TABLE 3

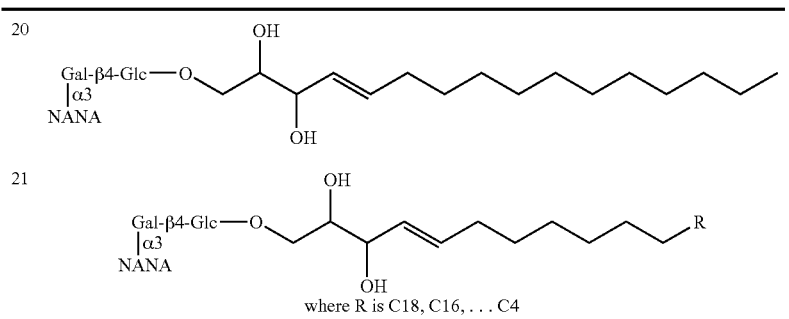

The invention further provides a synthetic ganglioside of formulae (Va), (Vb), (Vc) and (Vd):

In formulae (Va), (Vb), (Vc), and (Vd), as set forth above:

the saccharide is selected from the group consisting of a monosaccharide, a disaccharide, an oligosaccharide, a polysaccharide, an N-acetylated derivative thereof, and an N-deacylated derivative thereof; preferably, the saccharide is selected from the group consisting of:

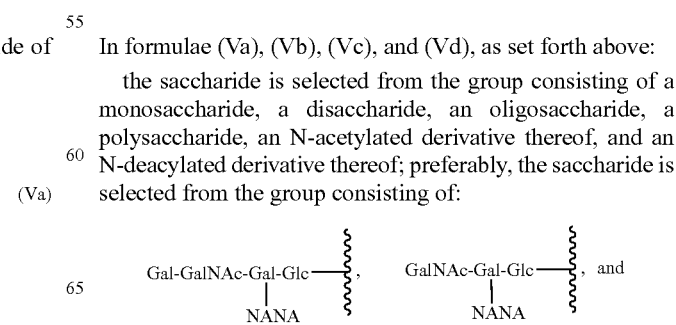

-continued

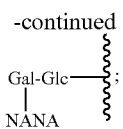

more preferably, the saccharide is:

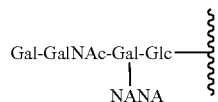

Z is O, S, or —NR$_1$;

X is H, —OR$_1$, —NR$_1$R$_2$, —SR$_1$, or —CHR$_1$R$_2$; preferably, —NR$_1$R$_2$;

R$_1$ and R$_2$ are independently H, —CH$_2$R$_3$, —CH(halo)$_2$, —C(=M)R$_3$, —C(=M)-p-R$_3$, —SO$_2$R$_3$, —SO$_3$, alkyl, aryl, arylalkyl, heteroaryl, heteroalkyl or haloalkyl; preferably, —CH(halo)$_2$ or —C(=M)R$_3$;

M is O, NR$_4$ or S;

R$_4$ is H, alkyl, aryl, arylalkyl, heteroaryl, heteroalkyl, or haloalkyl;

p is O, —NR$_4$, or S, where R$_4$ is as set forth above;

R$_3$ is H, alkyl, arylalkyl, haloalkyl, aryl, heteroaryl, or heteroalkyl;

Y is H, —OR$_1$, —SR$_1$, —NR$_1$R$_2$, alkyl, aryl, arylalkyl, heteroaryl, heteroalkyl, or haloalkyl, where R$_1$ and R$_2$ is as set forth above; preferably, —OR$_1$, where R$_1$ and R$_2$ is as set forth above; and R$_6$, R$_6$', R$_6$", R$_7$ and R$_8$ are independently H, alkyl, cycloalkyl, alkenyl, alkynyl, aryl, heterocycloalkyl heteroaryl, thioalkyl, thioaryl —CN, —NR$_9$R$_{10}$, C(=O)R$_9$, —C(=O)OR$_9$, or (=O)NR$_9$R$_{10}$, where R$_6$, R$_6$', R$_6$", R$_7$ and R$_8$ may be optionally substituted with at least one group selected from the group consisting of halo, haloalkyl, alkoxy, and thiohaloalkyl; and where R$_6$', R$_6$" and R$_7$, or R$_6$ and R$_7$, or R$_7$ and R$_8$, or R$_6$ and R$_8$, or R$_6$', R$_6$", R$_7$ and R$_8$, or R$_6$, R$_7$ and R$_8$ may each independently be taken together with the atoms to which they are attached to form a substituted cycloalkyl, heterocycloalkyl, aryl or heteroaryl group; preferably, where R$_6$', R$_6$" and R$_7$, or R$_6$ and R$_7$, or R$_7$ and R$_8$, or R$_6$ and R$_8$, or R$_6$', R$_6$", R$_7$ and R$_8$, or R$_6$, R$_7$ and R$_8$ may each independently be taken together with the atoms to which they are attached forms an optionally substituted aryl or heteroaryl; with the proviso that when R$_7$ of formula (Vb) is an alkyl group or a C$_{11}$ alkenyl group, X is not a —NH-fatty acid group and Y is not —OH;

R$_9$, R$_{10}$, and R$_{11}$ are independently alkyl, cycloalky, aryl, arylalkyl, heteroaryl, or heteroalkyl, where R$_9$, R$_{10}$, and R$_{11}$ may be optionally substituted, preferably substituted with at least one group selected from the group consisting of halo, haloalkyl, alkoxy, and thiohaloalkyl; and where R$_9$ and R$_{10}$ taken together with the nitrogen to which they are attached form a heterocyclic ring at least one heteroatom selected from N, O and S.

and all pharmaceutically acceptable salts, isomers, hydrates, prodrugs, and solvates thereof.

In a preferred embodiment of the invention, the

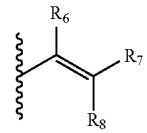

moiety of (Vb) is a conjugated hydrophobic moiety, including but not limited to, mono-, bi- and polycyclic aromatic and heteroaromatic rings systems, as defined herein. More preferably, the invention provides a synthetic ganglioside of the following formula:

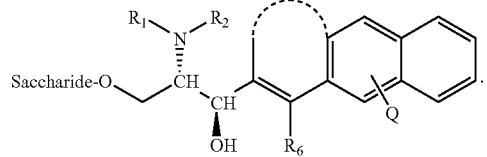

where at least one carbon of the

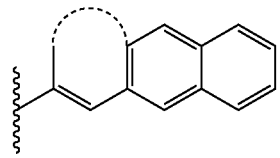

moiety may be replaced with a heteroatom selected from the group consisting of N, O and S and Q may be a substituent as defined herein including, but not limited to, halo, hydroxy, alkoxy, thio, thiol, hydrocarbon, and amino.

In another embodiment of the invention, the

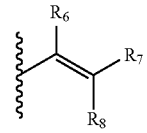

moiety of (Vb) is a cyclic moiety, including but not limited to, mono-, bi- and polycyclic ring systems, as defined herein Such cyclic ring systems may be either homocyclic or heterocyclic, or a mixture of both Further, such cyclic ring systems may be conjugated. Any such ring systems of the present invention may also be unsubstituted, or mono-, bi- or polysubstituted. Examples of synthetic gangliosides of the invention comprising such cyclic ring systems include:

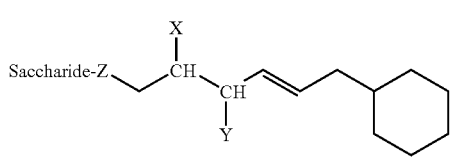

-continued

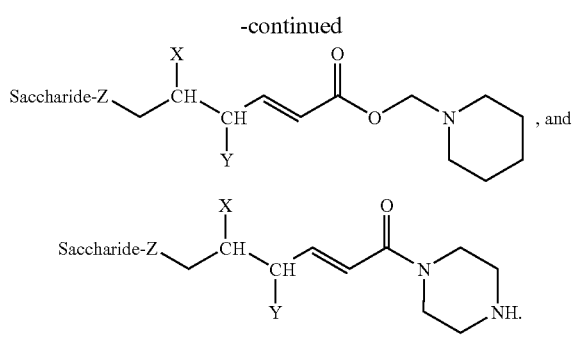

In yet another embodiment of the invention, the

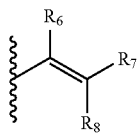

moiety of (Vb) is an aromatic moiety, including but not limited to, mono-, bi- and polycyclic aromatic ring systems, as defined herein. Such aromatic ring systems may be either homocyclic or heterocyclic, or a mixture of both. Such aromatic ring structures may also be unsubstituted, or mono-, bi- or polysubstituted. Examples of synthetic gangliosides of the invention comprising such aromatic moieties include:

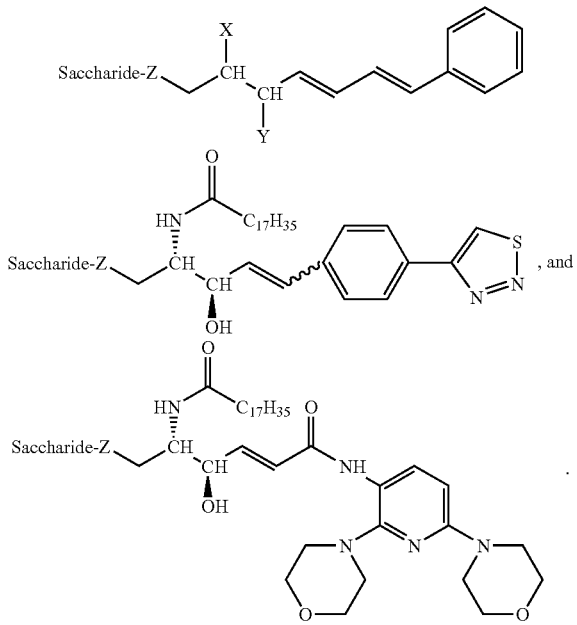

In still another embodiment of the invention, the

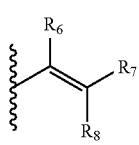

moiety of (Vb) is such that the double bond has been removed by simultaneously substituting $R_9$ for $R_6$ and $R_{10}$ for $R_8$, as defined herein. An example of such a substituted embodiment of the present invention is illustrated by

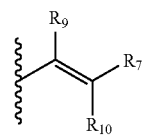

The invention further provides preferred compounds of formula (Vb) where the

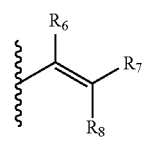

moiety is selected from the group consisting of:

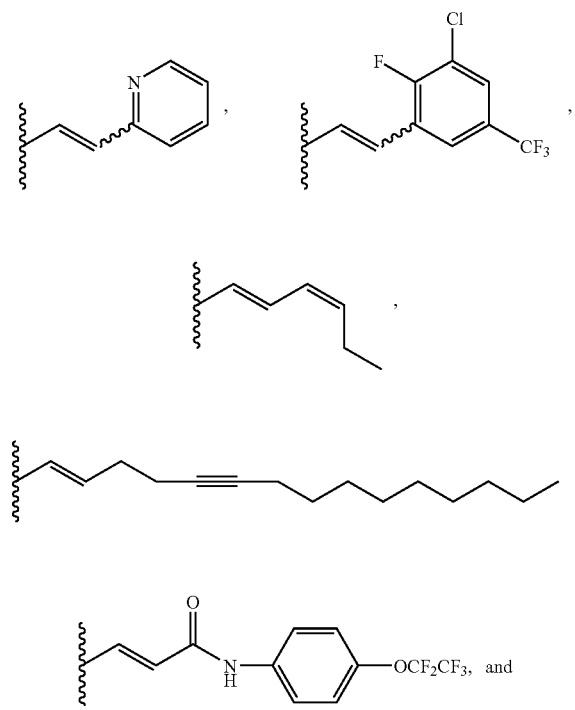

Preferred compounds of formula (Vb) include, but are not limited to:
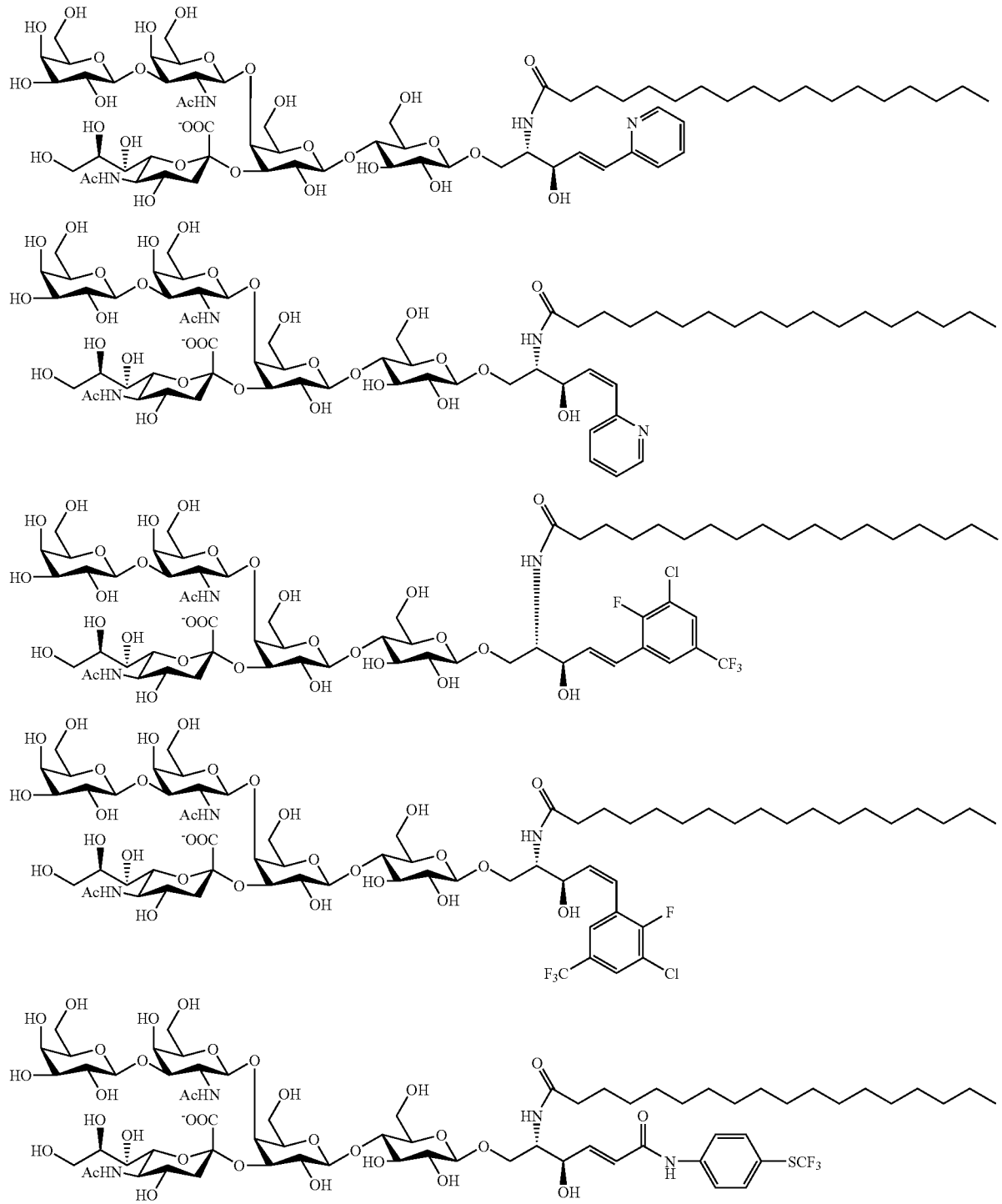

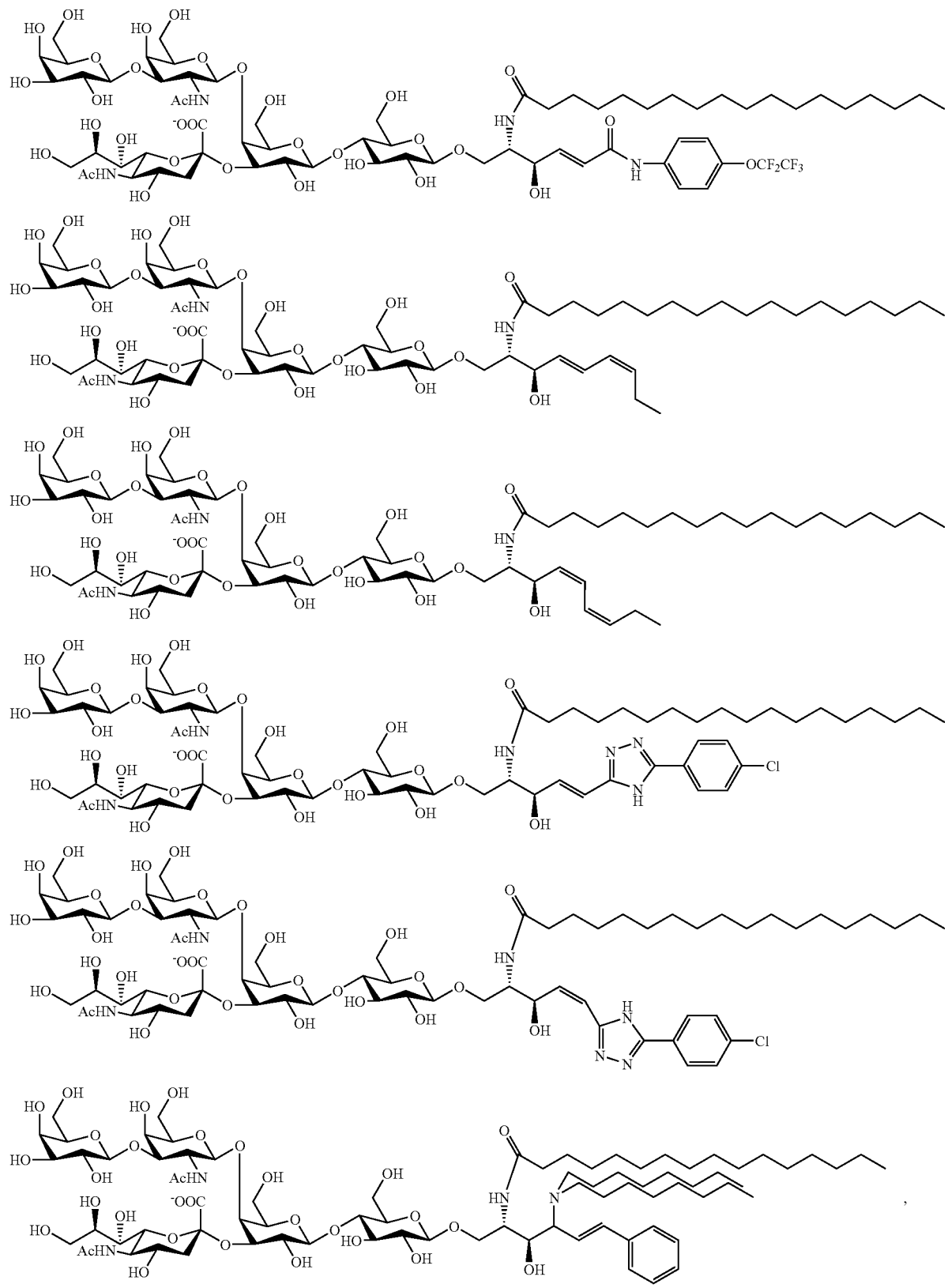

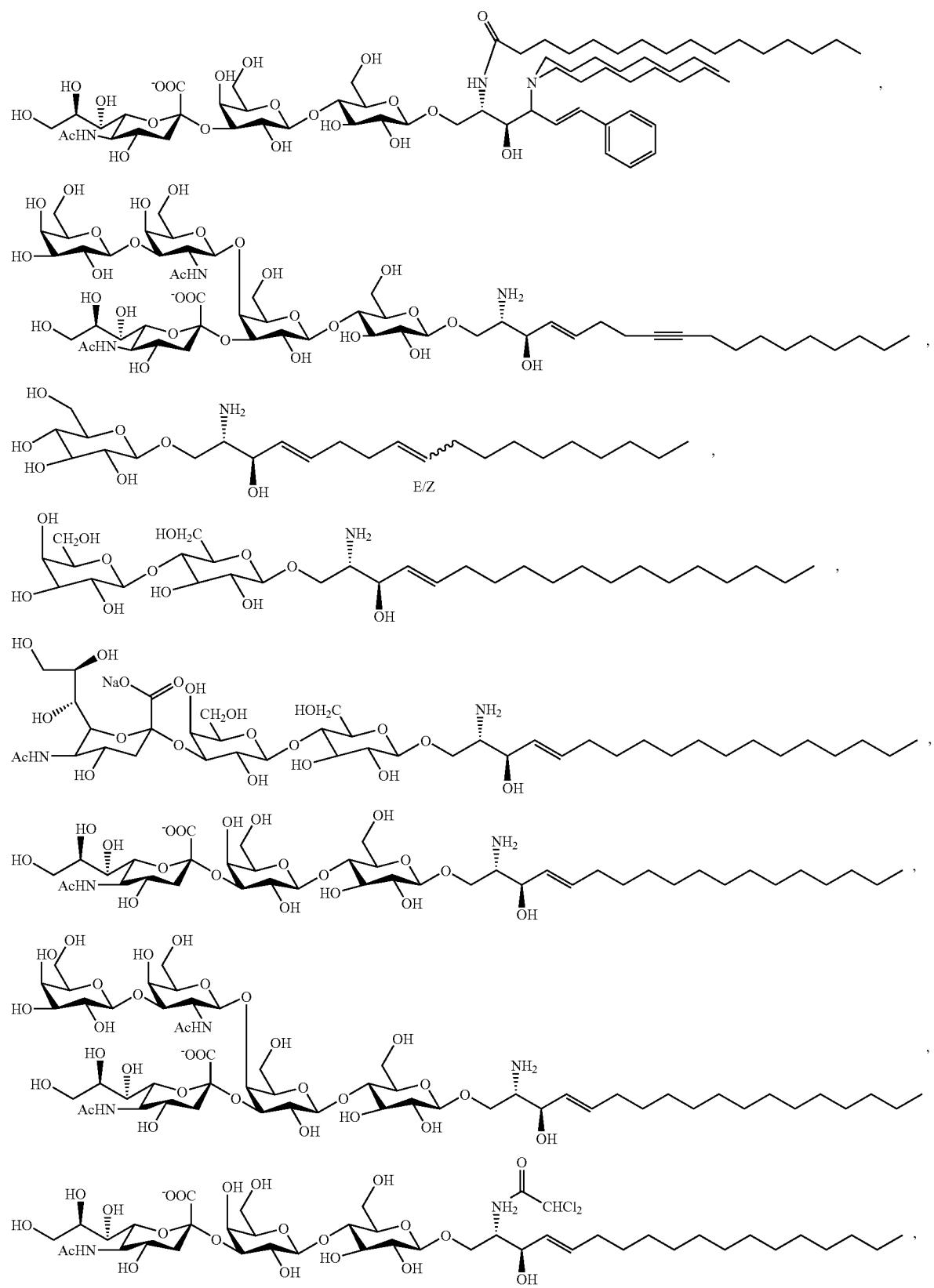

-continued

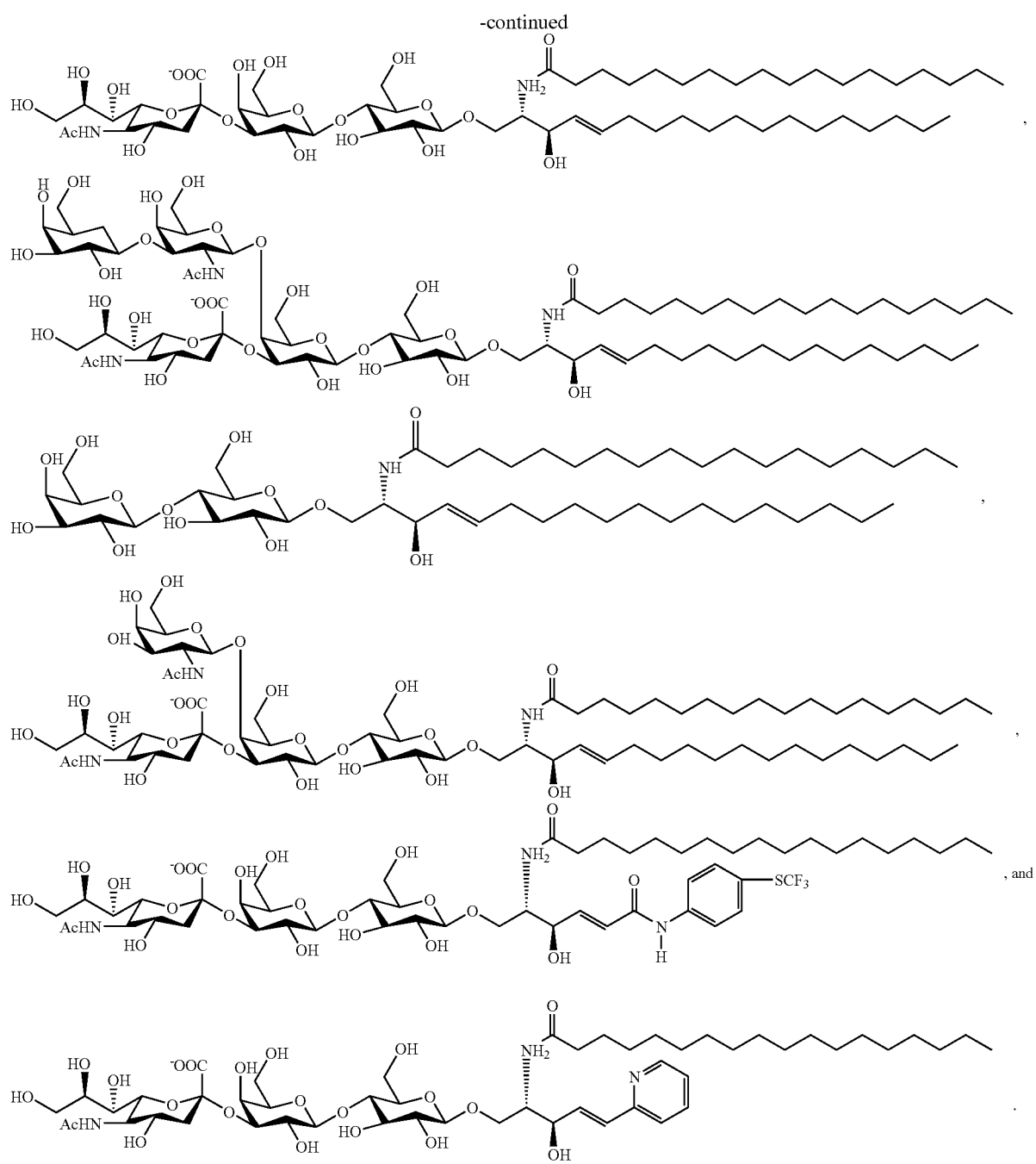

, and

The invention also encompasses all pharmaceutically acceptable isomers, salts, hydrates, solvates, and prodrugs of each of the compounds described above. In addition, such compounds can exist in various isomeric and tautomeric forms, and all such forms are meant to be included in the invention, along with pharmaceutically acceptable salts, hydrates, and solvates of such isomers and tautomers.

Methods of Preparation

According to the invention, synthetic ganglioside compounds of formulae (I) and (Va)-(Vd) may be prepared using, unless otherwise indicated, conventional methods and protocols in chemistry and enzymology known in the art. For example, compounds of the invention may be prepared by synthetic and enzymatic processes as outlined in Schemes 1-6 set forth below.

A. Method of Preparing Saccharide

The saccharide portion of the compounds of the invention may be prepared by any means known in the art including those methods described in U.S. Pat. Nos. 5,922,577, 6,284,493 and 6,331,418, each of which is incorporated herein in its entirety by reference. Preferably, the saccharide portion of the compounds of the invention is prepared enzymatically whereby a specific enzyme may be used to affect transfer of a monosaccharide from a donor molecule to an acceptor molecule, each as defined herein.

More specifically, disaccharides, oligosaccharides and polysaccharides, as found in the synthetic ganglioside compounds of the invention, may be prepared biosynthetically by use of glycosyltransferases. Such glycosyltransferase reactions may be carried out in the presence of an organic solvent, such as, for example, methanol, ethanol, dimethylsulfoxide, isopropanol, tetrahydrofuran, chloroform, and the like, either singly or in combination. Alternatively, such glycosyltransferase reactions may be conducted in a biological medium in vitro, such as a biological buffer, a cell lysate, or on a chromatographic support, wherein the glycosyltransferase is immobilized on the chromatographic support and the other components of the reaction mixture are contacted with the glycosyltransferase by contacting the components with the choromatographic support in an aqueous medium.

Glycosyltransferase-mediated synthesis of saccharides found in synthetic ganglioside compounds of the invention may also be conducted in vivo. For example, whole-cell expression systems may be used for glycosyltransferase-mediated synthesis. Cell types that may be used for expression of glycosyltransferases and concomitant production of saccharide structures include bacterial cells, yeast cells, and insect cells, as would be understood by one of skill in the art. The desired saccharide product can be isolated from the cell in which it was synthesized by lysis of the cell, or by isolation of cell culture medium when using a cell that secretes the saccharide product into the culture medium. The saccharide product may then be purified by means described elsewhere herein, or it may be used without further purification in a lysate or cell culture medium.

As would be understood by one of skill in the art, the enzyme used may vary depending upon the monosaccharide to be transferred. Examples of suitable enzymes include, but are not limited to, glycosyltransferases, trans-sialidases, and sialyltransferases. The choice of glycosyltransferase(s) used in a given synthesis method of the invention will depend upon the identity of the acceptor and donor molecules used as the starting material and the nature of the desired end product. A method of the invention can involve the use of more than one glycosyltransferase, where more than one saccharide is to be added. Multiple glycosyltransferase reactions can be carried out simultaneously, i.e., in the same reaction mixture at the same time, or sequentially.

To obtain sufficient amounts of glycosyltransferase for large-scale in vitro reaction, a nucleic acid that encodes a glycosyltransferase can be cloned and expressed as a recombinant soluble enzyme by methods known to one of ordinary skill in the art. The expressed enzyme may then be purified by means known to one of ordinary skill in the art, or it may be used without further purification in a lysate or cell culture medium.

By way of example, the saccharide moiety:

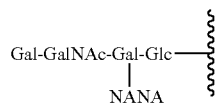

may be prepared by contacting an acceptor molecule containing a glucose (Glc) with a galactosyltransferase and a galactose (Gal) donor molecule to form:

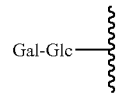

which in turn can be contacted with a trans-sialidase and a NANA donor molecule to form:

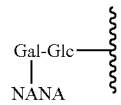

which in turn can be contacted with a N-acetylated galactose (GalNAe)-transferase and a GalNAc donor molecule to form:

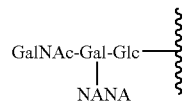

which in turn can be contacted with a galactosyltransferase and a galactose (Gal) donor molecule to form the desired saccharide:

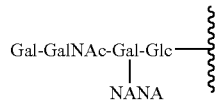

If the acceptor is a ceramide, the enzymatic step is typically preceded by hydrolysis of the fatty acid moiety from the ceramide; a fatty acid moiety can be reattached after completion of the glycosyltransferase reaction. The initial monosaccharide may be added, depending on the desired end product, either a ceramide glucosyltransferase (EC 2.4.1.80, for glucosylceramide) or a ceramide galactosyltransferase (EC 2.4.1.45, for galactosylceramide). For review of glycosphingolipid biosynthesis, see, e.g., Ichikawa and Hirabayashi (1998) Trends Cell Biol. 8:198-202. Ceramide glucosyltransferases are available from various sources. For example, the human nucleotide sequence is known (GenBank Accession No. D50840; Ichikawa et al. (1996) Proc. Nat'l. Acad. Sci. USA 93:4638-4643), so recombinant methods can be used to obtain the enzyme. The nucleotide sequence of the human ceramide galactosyltransferase also has been reported (GenBank Accession No. U62899; Kapitonov and Yu (1997) Biochem. Biophys. Res. Commun. 232: 449-453), and thus the enzyme is easily obtainable. The acceptor used in these reactions can be any of N-acylsphingosine, sphingosine and dihydrosphingosine. Suitable donor nucleotide sugars for the glycosyltransferase include UDP-Gc and CDP-Glc, while the galactosyltransferase typically uses UDP-Gal as a donor.

Methods of removing a fatty acid moiety from a glycosphingolipid are known to those of skill in the art Standard carbohydrate and glycosphingolipid chemistry methodology can be employed, such as that described in, for example, Paulson et al. (1985) Carbohydrate Res. 137: 39-62; Beith-Halahmi et al. (1967) Carbohydrate Res. 5: 25-30; Alais and Veyrieries (1990) Carbohydrate Res. 207: 11-31; Grudler and Schmidt (1985) Carbohydrate Res. 135: 203-218; Ponpipom et al. (1978) Tetrahedron Lett. 1717-1720; Murase et al. (1989) Carbohydrate Res. 188: 71-80; Kameyama et al. (1989) Carbohydrate Res. 193: c1-c5; Hasegawa et al. (1991) J. Carbohydrate Chem. 10: 439-459; Schwarzmann and Sandhoff (1987) Meth. Enzymol. 138: 319-341; Guadino and Paulson (1994) J. Am. Chem. Soc. 116: 1149-1150 (including supplemental material, which is also incorporated herein by reference). For example, hydrolysis of the fatty acid moiety can be effected by base hydrolysis. Once the glycosylation reactions are completed, the same or a different fatty acid can be attached to the product of the glycosylation reactions. Methods for coupling a fatty acid include those known in the art.

Another possible biosynthetic method for the synthesis of the saccharide portion of a compound of the invention is exemplified in Scheme 1 below. In a preferred embodiment, the acceptor molecule is non-immobilized. For example, the acceptor molecule may be free in solution or otherwise not associated with other acceptor molecules.

Additional saccharide residues may be added to a compound of the invention without prior modification of the glycosylation pattern of the glycosphingolipid starting material. Alternatively, the invention provides methods of altering the glycosylation pattern of a glycosphingolipid prior to adding the additional saccharide residues. If the starting glycosphingolipid does not provide a suitable acceptor for the glycosyltransferase which catalyzes a desired saccharide addition, one can modify the glycosphingolipid to include an acceptor by methods known to those of skill in the art.

For example, to provide a suitable acceptor for a sialyltransferase, a suitable acceptor can be synthesized by using a galactosyltransferase to attach a galactose residue to, for example, a GalNAc or other appropriate saccharide moiety that is linked to the glycosphingoid. In other embodiments, glycosphingoid-linked oligosaccharides can be first "trimmed," either in whole or in part, to expose either an acceptor for the sialyltransferase or a moiety to which one or more appropriate residues can be added to obtain a suitable acceptor. Enzymes such as glycosyltransferases and endoglycosidases are useful for the attaching and trimming reactions.

Figure 2:
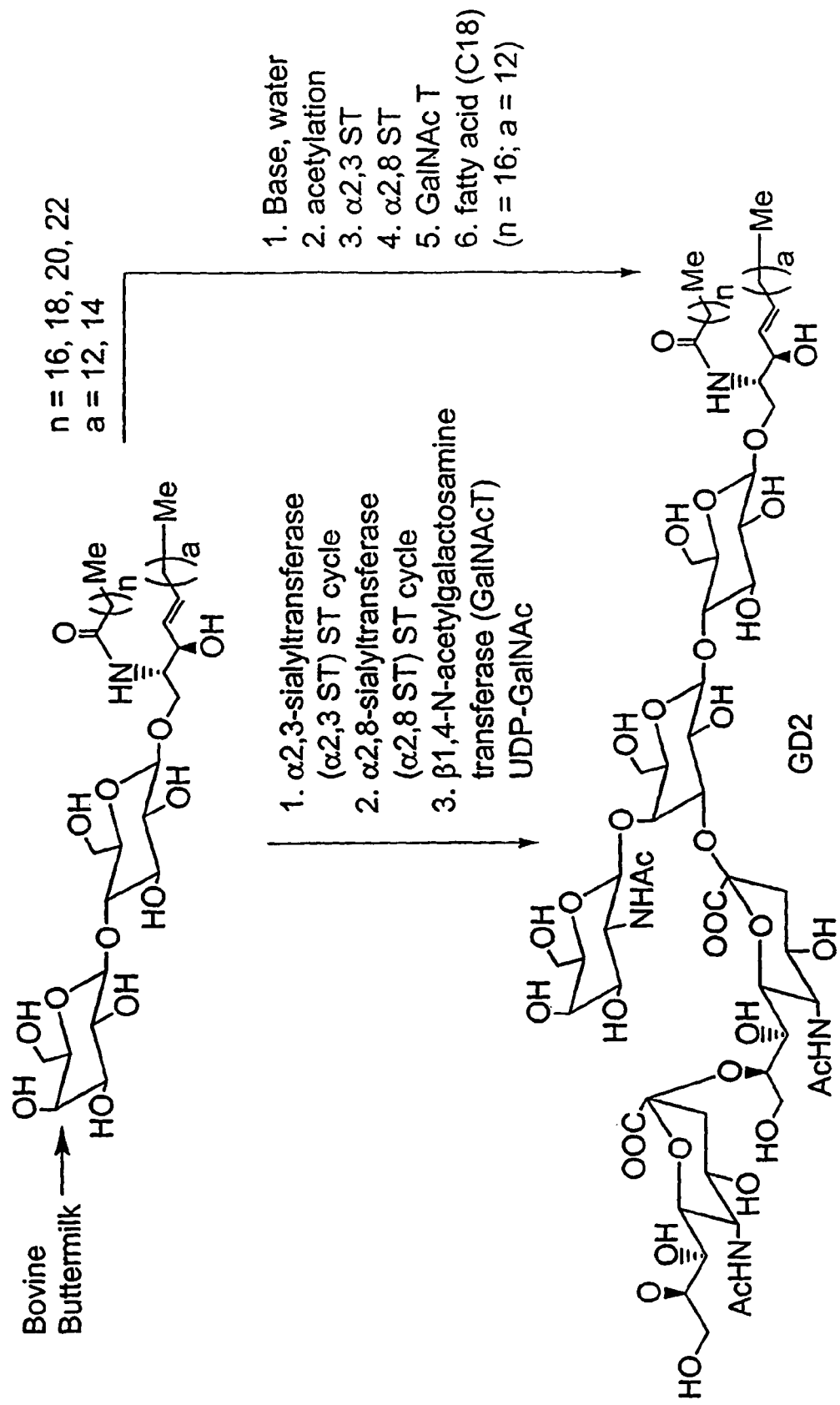
FIG. 2 shows a schematic diagram of two methods for synthesizing the ganglioside $GD_2$ from lactosylceramide obtained from bovine buttermilk.

Sialyltransferases and other glycosyltransferases can be used either alone or in conjunction with additional enzymes. For example, FIG. 2 shows a schematic diagram of two pathways for synthesis of the ganglioside $GD_2$ starting from lactosylceramide. Each pathway involves the use of two different sialyltransferases (an α2,3ST and an α2,8ST), as well as a GalNAc transferase. In the preferred pathway, the fatty acid is removed from the lactosylceramide by treatment with base (Step 1). Acetylation is then performed (Step 2), after which a sialic acid is attached to the galactose residue in an α2,3 linkage by an α2,3 sialyltransferase (Step 3). The sialylation steps are performed, preferably in the presence of an organic solvent as described herein, thereby driving the reaction nearly to completion. A GalNAc residue is then added to the galactose in a β1,4 linkage using a GalNAc transferase (Step 5). Finally, a fatty acid is added, e.g., by reaction with steroyl chloride, to complete the ganglioside (Step 6).

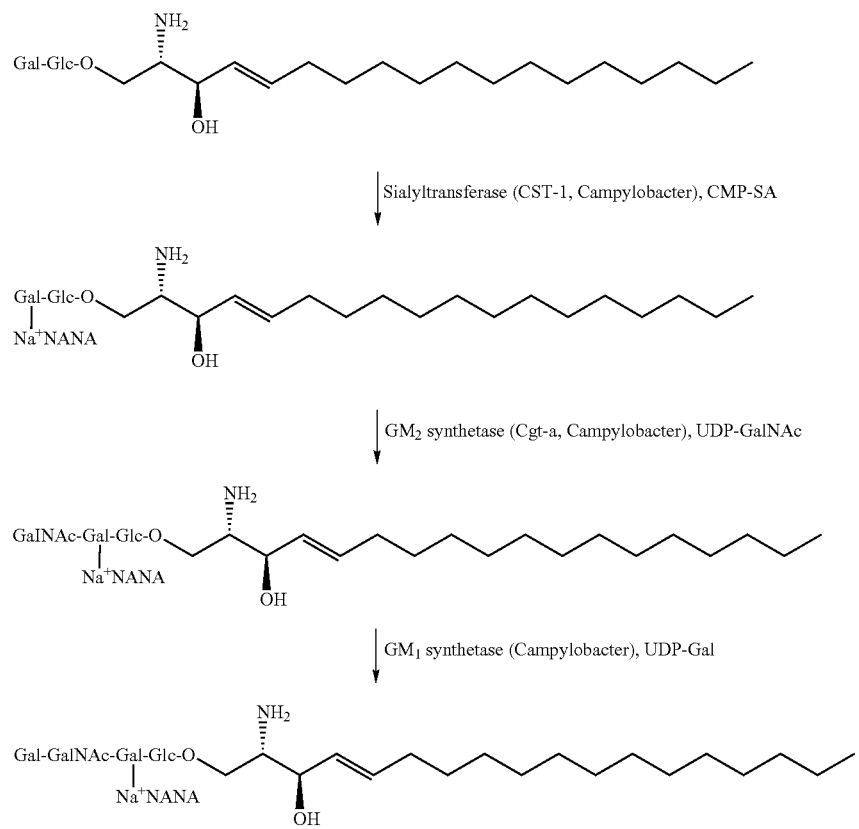

SCHEME 1

B. Method of Preparing Compounds of Formulae (I)-(Vd)
Compounds of the invention may be prepared by any means known in the art. Preferred synthetic pathways are illustrated in Schemes 2-5.
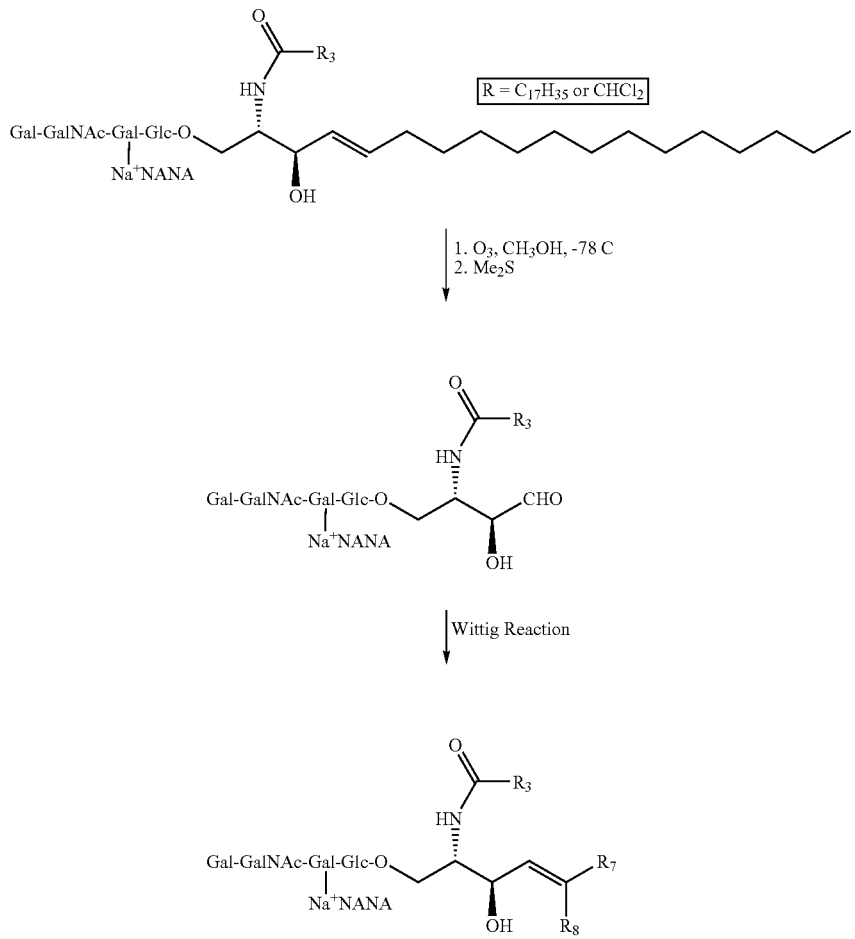
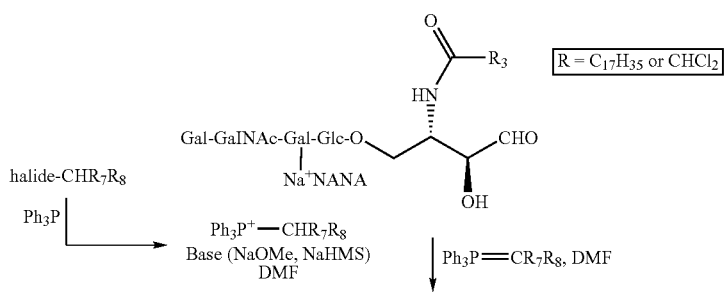

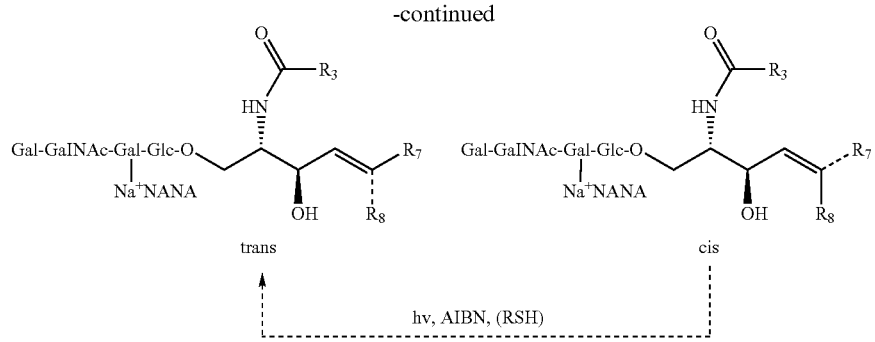

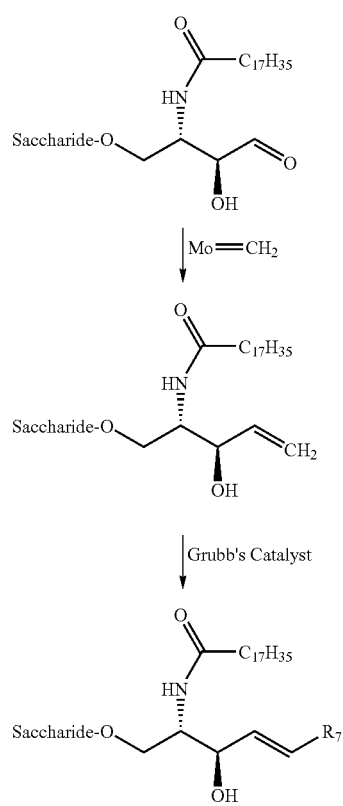

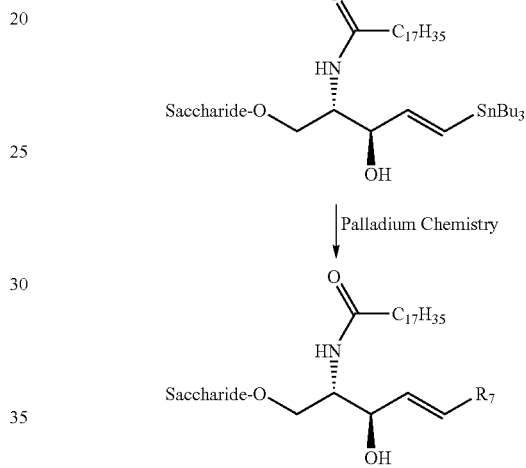

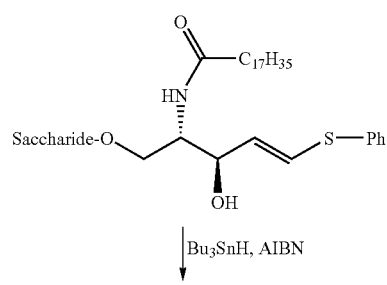

Once synthesized, the compounds of the invention may be isolated and purified by any means known in the art including, but not limited to, chromatography (e.g., thin, ion-exchange, column), filtration, membrane filtration (e.g., reverse osmotic membrane, nanfiltration), recrystallization, distillation, and the like.

A compound of the invention is useful in the field of neuroprotection. The term "neuroprotection" relates to any prophylaxis (pre-onset), treatment (on-set) and/or cure (post-onset) of indications resulting from the impairment or destruction of neuronal cells. Such indications include Parkinson's disease, ischemia, stroke, Alzheimer's, central nervous system disorders (e.g., spinal cord injury), multiple sclerosis, Huntington's disease, CABG, depression, anxiety, encephalitis, meningitis, amyotrophic lateral sclerosis, trauma, spinal cord injury, nerve injury, and nerve regeneration. A compound of the invention is also useful in the treatment of cancers in general, including liver, lung, colon, prostate, breast, pancreatic, and cancers of the brain, such as glioma and neuroblastoma. Further, a compound of the present invention is useful as an immunosuppressive and immunostimulatory agent, and has applications in organ transplantation, autoimmune disease, arthritis, Systemic Lupus Erythematosus, irritable bowel disease, radiation toxicity and inflammation, psoriasis, dermatitis, multiple sclerosis, trauma and sepsis.

A compound of the invention can be used to stimulate or suppress T-cells and B-cells, and can be used for antibody suppression or stimulation. Methods of stimulating and suppressing T-cells and B-cells is well-known in the art. Further, a compound of the invention may be used in a method to inhibit or activate membrane receptors, including G-protein coupled receptors, cell surface membrane receptor systems, and nuclear membrane receptors. A compound of the invention can further be used to treat type II diabetes and as an ethryopoeitin replacement.

A compound of the present invention is also useful as an inhibitor of platelet aggregation. Further, a compound of the present invention is useful in AIDS treatment, by inhibiting viral adhesion through G-protein coupled receptors, including CCRC5 and CXC4. A compound of the invention is also useful in the treatment of diseases such as Chagas disease, as well as diseases, disorders, and conditions described in U.S. Pat. Nos. 4,476,119, 4,593,091, 4,639,437, 4,707,469, 4,713,374, 4,716,223, 4,849,413, 4,940,694, 5,045,532, 5,135,921, 5,183,807, 5,190,925, 5,210,185, 5,218,094, 5,229,373, 5,260,464, 5,264,424, 5,350,841, 5,424,294, 5,484,775, 5,519,007, 5,521,164, 5,523,294, 5,677,285, 5,792,858, 5,795,869, and 5,849,717, each of which is incorporated by reference herein.

One possible mechanism of action of a compound of the invention is to stimulate nerve growth factors. Another possible mechanism of action of a compound of the invention is to inhibit growth of cancer cells, and in particular, neuroblastoma cells. For example, it has been shown that administration of ganglioside GM3 to murine neuroblastoma cells can inhibit the growth of the neuroblastoma cells (Zhang et al., 1995, Anticancer Res. 15:661-6). Ganglioside and ganglioside-like compounds of the present invention can be used in a similar inhibitory capacity.

According to the invention, isolated and purified compounds of the invention for use in the field of neuroprotection or cancer treatment are of an acceptable purity level. As would be understood by one of skill in the art, acceptable purity levels would depend upon the particular application. The compounds of the invention may be purified to levels ranging from about 80-100% pure, preferably, from about 90-100% pure, and more preferably about 95-100% pure.

Pharmaceutical Compositions

The invention further provides a pharmaceutical composition comprising at least one synthetic ganglioside compound of formulae (I) and (Va)-(Vd), each as set forth above, and a pharmaceutically acceptable carrier. Mixtures of synthetic gangliosides of the invention are also contemplated for use in pharmaceutical compositions.

Pharmaceutical compositions of the invention may be prepared for storage or administration by any means known in the art. For example, a pharmaceutical composition of the invention may be prepared by mixing a compound of the invention, preferably having a desired degree of purity, with a pharmaceutically or physiologically acceptable carriers or agent. The amount of active ingredient in these compositions is such that a suitable dosage in the range indicated is obtained.

A pharmaceutically acceptable carrier or agent may be any such carrier or agent known in the art. See, for example, in Remington's Pharmaceutical Sciences, Mack Publishing Co., (A. R. Gennaro edit. 1985). The pharmaceutical composition of the invention may further include a binder (e.g., acacia, corn starch or gelatin), an excipient (e.g., microcrystalline cellulose), a disintegrating agent (e.g., corn starch or alginic acid), a lubricant (e.g., magnesium stearate), a sweetening agent (e.g., sucrose or lactose), a buffer (e.g., phosphate, citrate, acetate and other organic acid salts), an antioxidant (e.g., ascorbic acid), a low molecular weight (less than about ten residues) peptide (e.g. polyarginine), a protein (e.g., serum albumin, gelatin, or immunoglobulins), a hydrophilic polymer (e.g., polyvinylpyrrolidinone), an amino acid (e.g., glycine, glutamic acid, aspartic acid, or arginine), a monosaccharide, a disaccharide, and other carbohydrates (e.g. cellulose or its derivatives, glucose, mannose or dextrins), a chelating agent (e.g., EDTA), sugar alcohol (e.g., mannitol or sorbitol), a counterion (e.g., sodium) and/or nonionic surfactants such as TWEEN, Pluronics or polyethyleneglycol. Additional acceptable adjuvants include those well known in the pharmaceutical field, and as described, for example, in Remington's Pharmaceutical Sciences, Mack Publishing Co., (A. R. Gennaro edit. 1985).

A compound or a pharmaceutical composition of the invention may be administered in solid or liquid form depending upon the desired application. Thus, a compound or pharmaceutical composition of the invention may be administered in solid form such as, for example, tablets, capsules, suppositories, in liquid form such as, for example, elixirs for oral administration, sterile solutions, sterile suspensions or injectable administration, and the like, or incorporated into shaped articles. A compound or a pharmaceutical composition of the invention may also be administered as sustained release and timed release formulations. Other modes of administration of a compound or composition of the invention include, but not limited to, implantable medical devices (e.g., stents), inhalable formulations, sprays, transdermal, liposomes, gels, intracraneal, and intrathecal.

A compound or pharmaceutical composition of the invention, especially when administered in capsule form, may also contain a liquid carrier such as, for example, water, saline, or a fatty oil Other materials of various types may be used as coatings or as modifiers of the physical form of the compound or pharmaceutical composition. For example, dissolution or suspension of the active compound of the invention in a vehicle such as an oil or a synthetic fatty vehicle like ethyl oleate, or into a liposome may be desired.

According to the invention, such materials as well as compounds of the invention are nontoxic to the recipients at the dosages and concentrations employed, i.e. are pharmaceutically acceptable.

In general, a compound of the invention, alone or as part of a pharmaceutical composition as described herein, may be used as a diagnostic or therapeutic agent for the prevention and/or treatment of disorders of the nervous system including neurological diseases such as, for example, Parkinson's disease, CABG, Alzheimer's Disease, and stroke. Further, a compound of the invention, alone or as part of a pharmaceutical composition as described herein, may be used as a therapeutic agent for the treatment of certain types of cancer, including neuroblastoma.

Compounds and pharmaceutical compositions of the invention are suitable for use alone or as part of a multi-component treatment regimen in combination with other therapeutic or diagnostic agents such as, for example, other synthetic gangliosides of the invention, natural gangliosides, other synthetic gangliosides, anti-inflammatory compounds, analgesics, other neurotrophic factors (e.g., growth factors). Coadministered compounds and agents may act in a synergistic fashion to enhance the neuroprotective activity of the compound of the invention.

The compounds and pharmaceutical compositions of the invention may be utilized in vivo, ordinarily in mammals such as primates, such as humans, sheep, horses, cattle, pigs, dogs, cats, rats and mice, or in vitro. The biological properties, as described above, of the compounds of the invention can be readily characterized by methods that are well known in the art including, for example, in vitro screening protocols and in vivo studies to evaluate the neuroprotective activity of the tested compound or pharmaceutical composition.

Subjects (animals or humans), preferably mammalian, in need of treatment may be administered a therapeutically effective amount, i.e., a dosage that will provide optimal efficacy, of a compound of the invention, alone or as part of pharmaceutical composition. As would be recognized by those of skill in the art, a "therapeutically effective amount" and mode of administration will vary from subject to subject and thus will be determined on a case by case basis. Factors to be considered include, but are not limited to, the subject (e.g. mammal) being treated, its sex, weight, diet, concurrent medication, overall clinical condition, the particular compounds employed, and the specific use for which these compounds are employed. Therapeutically effective amounts or dosages may be determined by either in vitro or in vivo methods. In general, a "therapeutically effective amount" of a compound or composition is an amount that will result in the prophylaxis, treatment or cure of neuronal cell disorders. For example, a therapeutically effective amount of a compound or composition of the invention in the prophylaxis, treatment or cure of Parkinson's disease will be that amount that results in slower progression of the disease and/or development of motor skills. A therapeutically effective amount of a compound or composition of the invention in the prophylaxis, treatment or cure of Alzheimer's disease will be that amount that results in, for example, improvement of the subject's memory. A therapeutically effective amount of a compound or composition of the invention in the prophylaxis, treatment or cure of the lasting effects of eschemia/stroke will be that amount that results in, for example, reduction of loss of neurological function (e.g., speech, motor, etc.) and/or improvement of sympathetic or parasympathetic pathways.

Modes of administration include those known in the art including, but not limited to, oral, injection, intravenous (bolus and/or infusion), subcutaneous, intramuscular, colonic, rectal nasal and intraperitoneal administration. Preferably, compounds of the invention, alone or as part of a pharmaceutical composition are taken orally.

For injection by hypodermic needle, it may be assumed the dosage is delivered into the body's fluids. For other routes of administration, the absorption efficiency may be individually determined for each compound of the invention by methods well known in pharmacology. Accordingly, as would be understood by one of skill in the art, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, a compound of the invention is administered at lower dosage levels, with dosage levels being increased until the desired effect is achieved.

A typical dosage might range from about 0.1 mg/kg to about 1000 mg/kg, preferably from 0.1 mg/kg to about 100 mg/kg, more preferably from about 0.1 mg/kg to about 30 mg/kg, more preferably from about 0.1 mg/kg to about 10 mg/kg, and more preferably 0.1 mg/kg to about 3 mg/kg. Advantageously, the compounds of the invention, alone or as part of a pharmaceutical composition, may be administered several times daily, and other dosage regimens may also be useful. A compound of the invention may be administered on a regimen in a single or multidose (e.g. 2 to 4 divided daily doses) and/or continuous infusion.

A compound of the invention, alone or as part of a pharmaceutical composition, for administration may be sterilized prior to administration. Sterility may be readily accomplished by filtration through sterile membranes such as 0.2 micron membranes, or by other conventional methods. A compound of the invention, alone or as part of a pharmaceutical composition, typically may be stored in lyophiliced form or as an aqueous solution. pH may be a factor for certain modes of administration. In such instances, the pH typically will range between about 2-10, preferably, between about 5-8, more preferably 6.5-7.5, i.e., physiological pH.

Screening Protocols

The compounds and pharmaceutical compositions of the invention may be utilized in vivo, ordinarily in mammals such as primates, such as humans, sheep, horses, cattle, pigs, dogs, cats, rats and mice, or in vitro. The effectiveness of the compounds of the invention as neuroprotective agents may be determined using screening protocols known in the art For example, the biological properties, as described above, of the compounds of the invention can be readily characterized by methods that are well known in the art including, for example, in vitro screening protocols (e.g. cell culture (MPTP (rat ventral mesophenthalic cells), NMDA (mouse primary cortical neurons), ceramide (neuroblastoma-human)), CACO-2 (oral absorption), RBC lysis) and in vivo studies (e.g. mouse and primate MPTP toxicity studies (SP, IV, and/or oral) for effectiveness in the treatment of Parkinson's, rat Stoke studies for effectiveness for treatment of neural damage due to stroke or CABG, and dog studies for treatment of CABG) to evaluate neuroprotective efficacy.

In the cell based assays, as described herein, the compounds of the invention exhibited 50-100% greater neuroprotective activity at lower concentrations ranging between about 0.1 to about 1 µM.

The invention is now described with reference to the following Example. This Example is provided for the purpose of illustration only and the invention should in no way be construed as being limited to this Example, but rather should be construed to encompass any and all variations which become evident as a result of the teaching provided herein.

EXPERIMENTAL EXAMPLES

Example 1

General Procedure for Preparing the $GM_1$ Aldehyde $GM_1$ (2.5 g, 1.62 mmol) was dissolved in 2500 mL of methanol. This solution was cooled to −70° C. and ozone bubbled through the solution until the light blue color did not disappear (about 30 mins). The ozone was removed by bubbling nitrogen through the reaction mixture until the solution became colorless. Then, 80 mL of dimethylsulfide was added and the resulting mixture was stirred at room temperature for 2 h. The solvent was evaporated with nitrogen to dryness. The residue was co-evaporated with toluene (50 mL) and the residue dried on a high vacuum pump for 1 h to yield a white solid containing the aldehyde.

Example 2

Wittig Reaction Preparation of

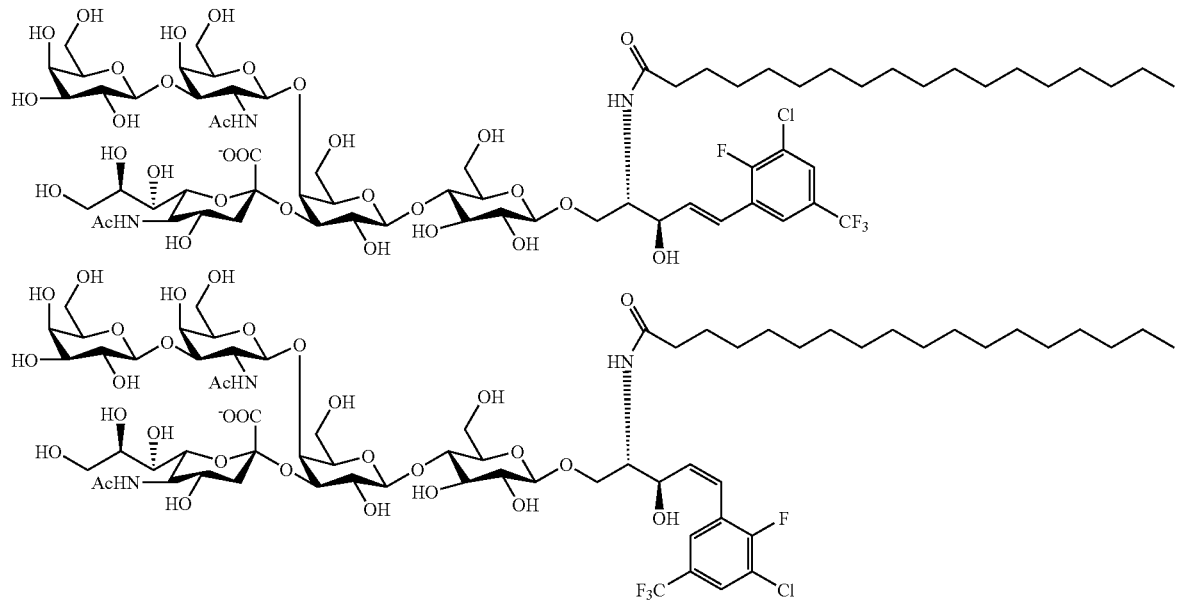

A suspension containing 3-chloro-2-fluoro-5-(trifluoromethyl)benzyltriphenylphosphonium bromide (2.58 g, 4.66 mmol), dimethylformamide (DMF) (50 mL) was cooled to −40° C. and 1M potassium tert-butyloxide in tert-butylalcohol solution (4.49 mL) was then added. After 10 minutes, this reaction mixture was added slowly to a solution of aldehyde dissolved in DMF (200 mL) and cooled to −40° C. After addition was complete, the reaction mixture was sired at room temperature for 1 h. The reaction mixture was then concentrated on a rotovap and the residue chromatographed (silica, $CHCl_3$/MeOH 3:1 then, MeOH/$H_2O$/$NH_4OH$ 60:40:7:1) to afford 1.5 g (60% yield) of the desired product as a ~70/30 cis/trans mixture. ESI-MS; calcd for $C_{67}H_{106}ClF_4N_3O_{31}$, 1559; found 1558 [M−1]⁻. $^1$H-NMR (500 MHz, 95% DMSO-$d_6$+5% $D_2O$) δ 7.98 (d, J 6.0 Hz, 2H), 7.84 (d, J 6.0 Hz, 1H), 7.82 (d, J 5.5 Hz, 2H), 7.60 (d, J 5.5 Hz, 1H), 7.34 (d, J 9.5 Hz, 2H), 6.64 (d, J 16 Hz, 1H), 6.48 (d, J 11.5 Hz, 2H), 5.93 (dd, J 11.5/11.5 Hz, 2H), 4.79 (d, J 8.5 Hz, 2H), 4.27 (d, J 8.0 Hz, 2H), 4.21 (d, J 8.5 Hz, 2H), 3.00-4.00 (m), 1.98 (m, 2H), 1.86 (s, 3H, $COCH_3$), 1.78 (s, 3H, $COCH_3$), 1.25 (m), 0.83 (t, 3H, $CH_3$).

Example 3

Wittig Reaction Preparation of

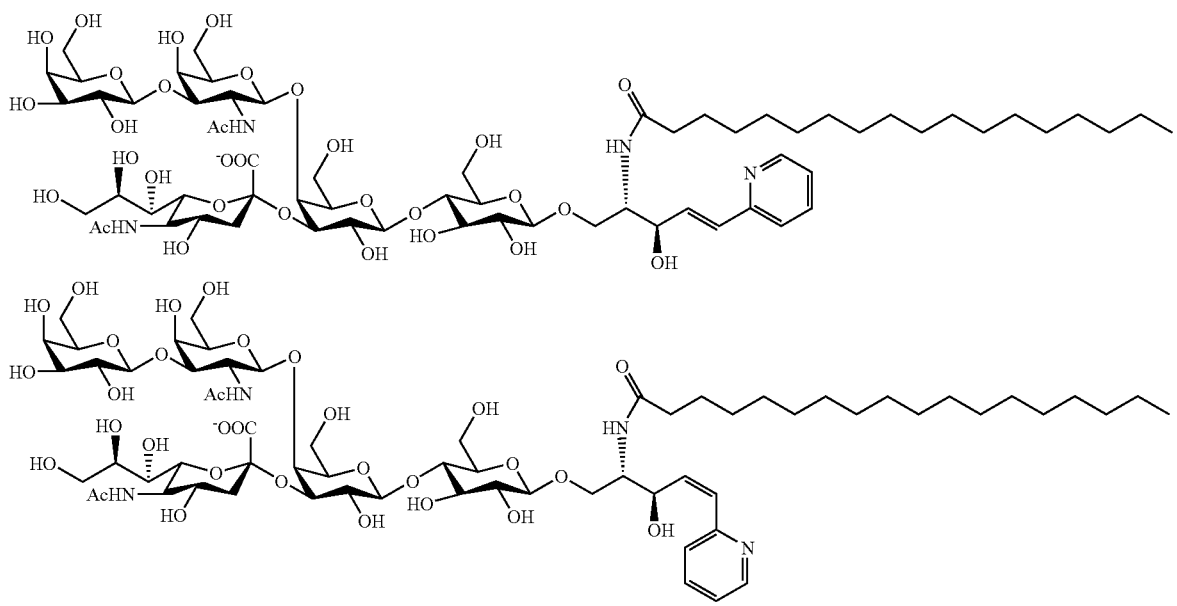

The Wittig procedure of Example 2 was followed except that the starting ylide was changed. The desired product was obtained as a white solid, (43% yield). ESI-MS; calcd for $C_{65}H_{108}N_4O_{31}$, 1440; found 1439 [M−1]⁻. ¹H-NMR (500 MHz, 95% DMSO-$d_6$+5% $D_2O$) δ 8.46 (d, J 4 Hz, 1H), 7.70 (dd, J 6.5 and 9.6 Hz, 1H), 7.37 (d, J 8.0 Hz, 1H), 7.18 (dd, J 5.0 and 5.0 Hz, 1H), 6.64 (dd, J 15.5 and 6.0 Hz, 1H), 6.57 (d, J 15.5 Hz, 1H), 4.82 (d, J 8.5 Hz, 1H), 4.27 (d, J 8.0 Hz, 1H), 4.18-4.22 (2d, 2H), 3.10-3.93 (m), 2.02 (t, 2H), 1.86 (s, 3H, $COCH_3$), 1.75 (s, 3H, $COCH_3$), 1.36 (m, 2H), 1.22 (s), 1.06 (m, 2H, $CH_2$), 0.83 (t, 3H, $CH_3$).

Example 4

Wittig Reaction Preparation of

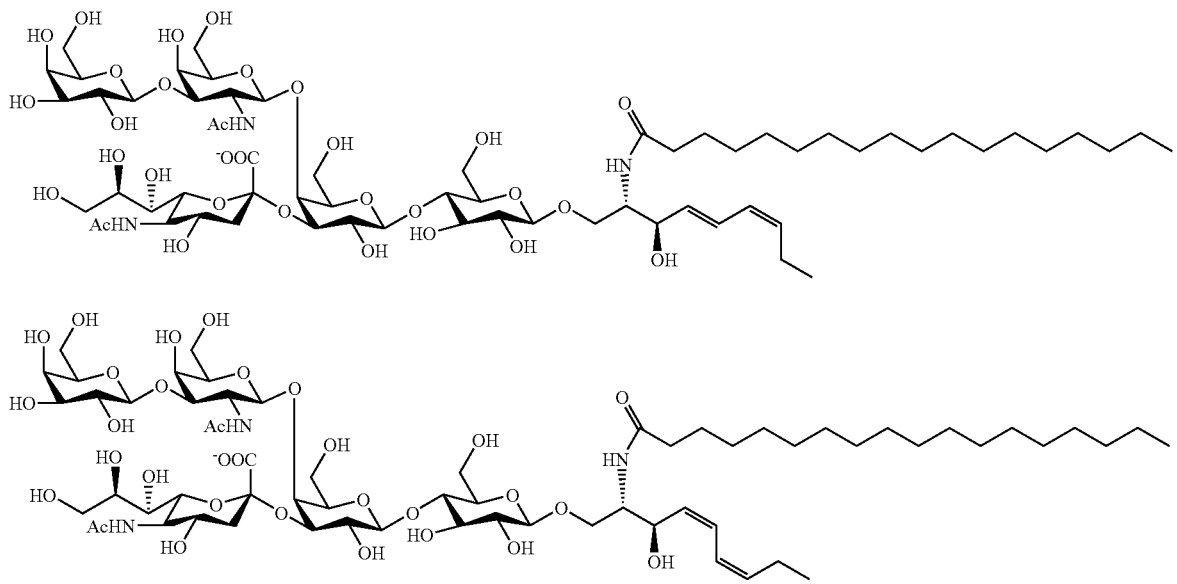

The Wittig procedure of Example 2 was followed except that the starting ylide was changed. The desired product was obtained as a solid (21% yield), as a 50/50 cis/trans mixture. ESI-MS; calcd for $C_{64}H_{111}N_3O_{31}$, 1417; found [M−1]⁻.

Example 5

Wittig Reaction Preparation of

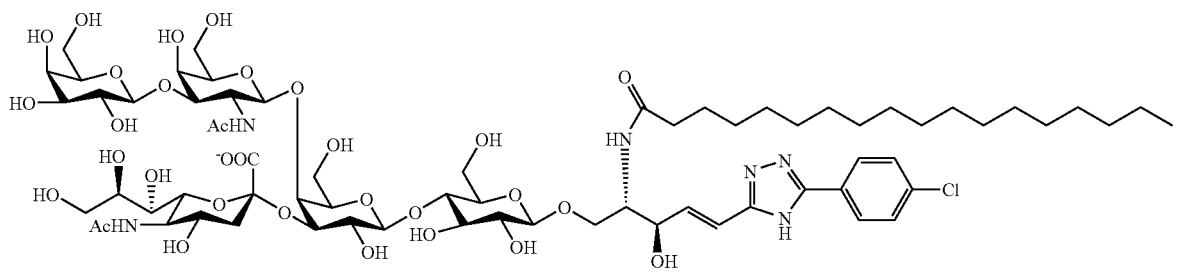

The Wittig procedure of Example 2 was followed except that the starting ylide was 10 changed. The desired product was obtained as a solid (45% yield). ESI-MS; calcd for $C_{68}H_{109}ClN_6O_{31}$ 1540; found 1539 [M−1]⁻. ¹H-NMR (500 MHz 95% DMSO-$_6$+5% $D_2O$) δ 8.00 (d, J 9.0 Hz, 2H), 7.50 (d, J 9.0 Hz, 2H), 4.80 (d, J 8.5 Hz, 1H), 4.26 (d, J 8.0 Hz), 4.22 (d, J 7.5 Hz, 1H), 4.19 (d, J 8.0 Hz, 1H), 3.05-4.00 (m), 2.02 (m, 2H), 1.87 (s, 3H, $COCH_3$), 1.75 (s, 3H, $COCH_3$), 1.21 (s), 0.83 (t, J 6.5 Hz, $CH_3$).

Example 6

Wittig Reaction Preparation of

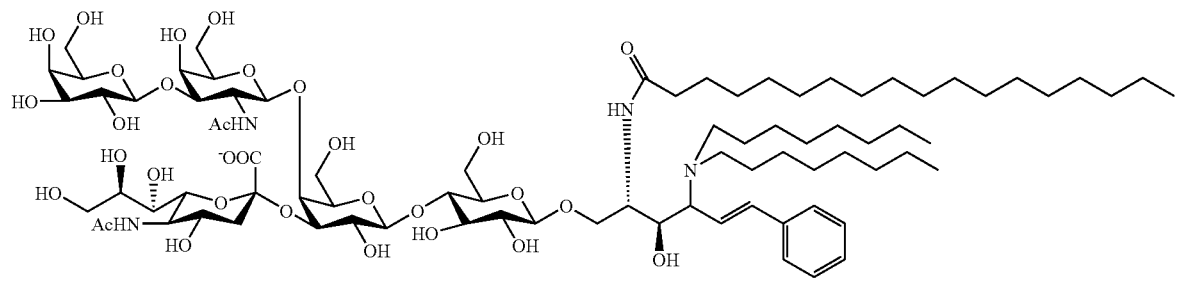

The GM$_1$ aldehyde (20 mg, 0.013 mmol) of Example 1 and dioctylamine (6 mg, 0.024 mmol), was added with stirring to 2.5 mL of dimethylformamide (DMF) at room temperature. Then trans-2-phenylvinylboronic acid (9 mg, 0.045 mmol) in methanol (5 mL) was added. The resulting solution was stirred at room temperature for three days. The reaction mixture was then concentrated to dryness on a rotovap and the residue purified by solid phase extraction using a 1 g HAX cartridge. The eluant was then purified using HPLC to afford 9.5 mg (43% yield) of white solid. ESI-MS; cacld for $C_{83}H_{144}N_4O_{31}$, 1693; found 1692 [M−1]$^-$. $^1$H-NMR (500 MHz, 95% DMSO-d$_6$+5% D$_2$O) δ 8.05 (d, J 3.0 Hz, 1H), 7.70 (m 5H), 6.40 (m, 1H), 6.25 (dd, J 9.0 and 16 Hz, 1H), 4.80 (d, J 8.5 Hz, 1H), 4.28 (d, J 8.0 Hz, 1H), 4.22 (d, J 8.0 Hz, 1H), 4.16 (d, 4.2 Hz, 1H), 3.00-4.00 (m), 2.10 (m, 2H), 1.86 (s, 3H, COCH$_3$), 1.60 (s, 3H, COCH$_3$), 1.19 (s), 0.83 (t, 3H, CH$_3$).

Example 7

MPTP/VMC Assay (In Vitro) for Evaluation of Neuroprotective Efficacy

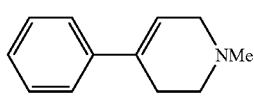

1-Methyl-4-phenyl-1,2,3,6-tetrahydro-pyridine ("MPTP")

Ventral Mesophenthalic Cells (VMCs) are isolated from fetal rat brain stems (15 days old). Cells are cultured for several days (48 well plates) with controls on every plate. Cells are treated with MPTP (10 μM for 24 hours which results in 30-50% cell death. Toxin is then removed. Cells are then treated with a compound of the invention in DMSO. After 24 hours, a tyrosine hydroxylase immuno-stain and cell count is performed.

The controls are MPTP (10 μM-30-50% cell kill) and GM$_1$ (30 μM) or LIGA-20 (10 μM)-30-50% protection.

Example 8

Sialylation of Lyso-Lactosyl Ceramide

This Example describes the reaction conditions for sialylation of lyso-lactosyl ceramide. Lactosylceramide was obtained from bovine buttermilk and the fatty acid moiety removed by base hydrolysis to form lyso-lactosyl ceramide. A mixture of the lyso-lactosyl ceramide (1.0 mg, 1.6 μmol) and CMP-sialic acid (2.46 mg, 65% purity, 2.40 μmol in HEPES buffer (200 mM, containing 8% MEOH, pH 7.5, 50 μL) was sonicated for twenty minutes. α2,3 sialyltransferase (10 μL, 5 U/mL, 50 mU) was then added followed by alkaline phosphatase (1 μL, 1.0×10$^5$ U/mL, 100 U). The reaction mixture was kept at room temperature. After one day, a further portion of α2,3 sialyltransferase (10 μL, 5 U/mL, 50 mU) was added. After four more days, an additional portion of α2,3 sialyltransferase (10 μL, 5 U/mL, 50 mU) was added. After an additional one day at room temperature, thin layer chromatography indicated that the reaction was nearly complete.

Example 9

Synthesis of GM2 from Lactosylceramide Obtained from Bovine Buttermilk

A schematic diagram of showing two pathways for synthesis of the ganglioside GM$_2$ from lactosylceramide obtained from bovine buttermilk is shown in FIG. 1. In the pathway shown at left, the fatty acid is not removed from the lactosylceramide prior to sialylation, and the reaction is not carried out in the presence of an organic solvent. The reaction at right, in contrast, is carried out in the presence of an organic solvent, and with removal of the fatty acid.

First, the fatty acid is hydrolyzed from the lactosylceramide by treatment with a base and water (Step 1). A sialic acid residue is then added by enzymatic transfer to the galactose residue using an α2,3 sialyltransferase, preferably an ST3GalIV (Step 2). This reaction can be carried out in the presence of an organic solvent. A GalNAc residue is then attached to the galactose in a β1,4 linkage using a GalNAc transferase (Step 3); this step may or may not be carried out in the presence of an organic solvent Finally, the fatty acid moiety is reattached to the sphingosine to obtain the desired GM$_2$ ganglioside. The reaction typically proceeds nearly to completion due to the presence of an organic solvent during the sialylation.

Example 10

Synthesis of Gangliosides from Plant Glucosyl Ceramide

Figure 3:
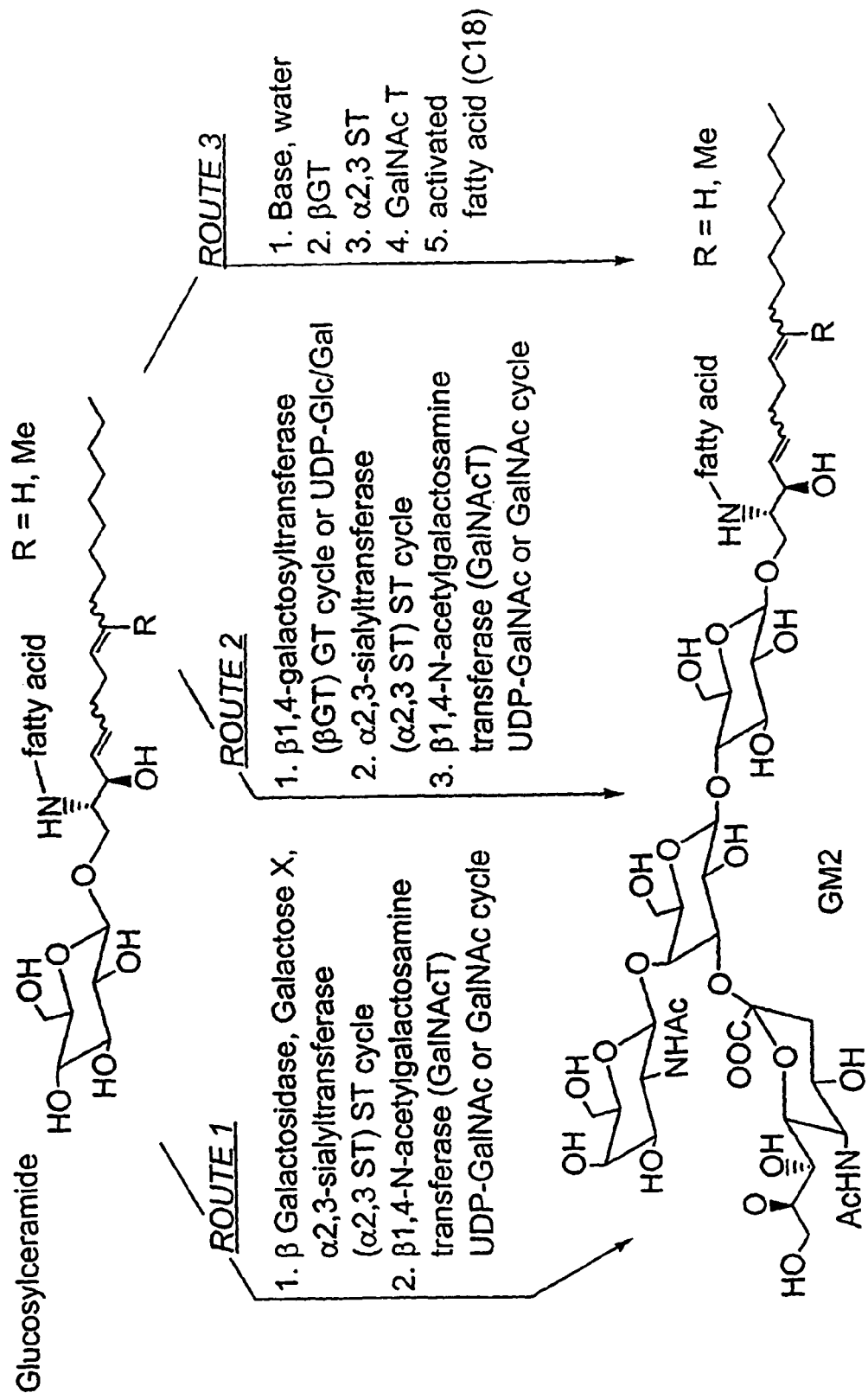
FIG. 3 shows three routes for synthesizing a GM2 ganglioside using a plant glucosylceramide as the starting material.

This Example describes three alternative procedures for the synthesis of the GM$_2$ ganglioside using plant glucosylceramide as the precursor (FIG. 3). In Route 1, β1,4-galactosidase is used to catalyze the transfer of a Gal residue to the glycosylceramide. Simultaneously, an α2,3-sialyltransferase is used in a sialyltransferase cycle to link a sialic acid residue to the Gal. Next, a β1,4-GalNAc transferase is added to the reaction mixture, either with UDP-GalNAc or as part of a GaAc transferase cycle. In this step, the GalNAc residue is linked to the Gal residue in an α2,3 linkage.

Route 2 differs from the synthesis shown in Route 1 in that the addition of the Gal to the glycosylceramide is catalyzed by a β1,4-galactosyltransferase enzyme, using either a galactosyltransferase cycle or UDP-Glc/Gal as the acceptor sugar. Sialylation and addition of GaCNAc are carried out as described above to obtain $GM_2$.

In Route 3, the fatty acid is first removed by treatment with aqueous base prior to the glycosyltransferase steps. The galactosylation, sialylation, and GalNAc transferase reactions are carried out as in Route 2. Following the addition of the GalNAc residue, a fatty acid is linked to the molecule. The fatty acid can be the same as that originally found on the plant glucosylceramide, or can be different. In the example shown in FIG. 4, an activated $C_{18}$ fatty acid is used, resulting in the synthesis of $GM_2$. Greater efficiency is generally observed when the fatty acid is removed prior to the glycosylation reactions.

Example 11

Synthesis of Ganglioside $GM_2$ from Glycosylceramide

Figure 4:
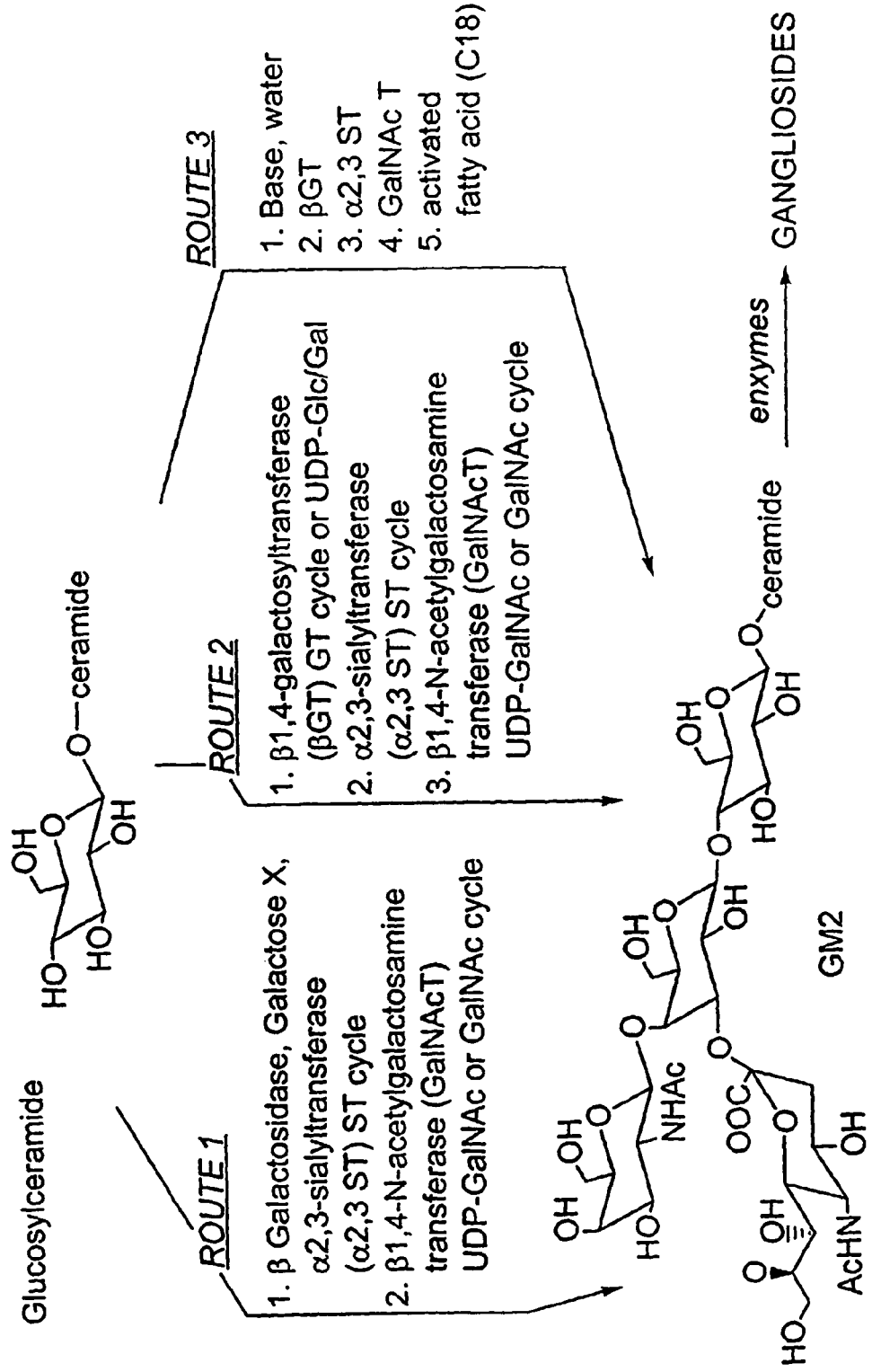
FIG. 4 shows three routes for synthesizing GM2 and other gangliosides starting from a glucosylceramide.
Figure 5:
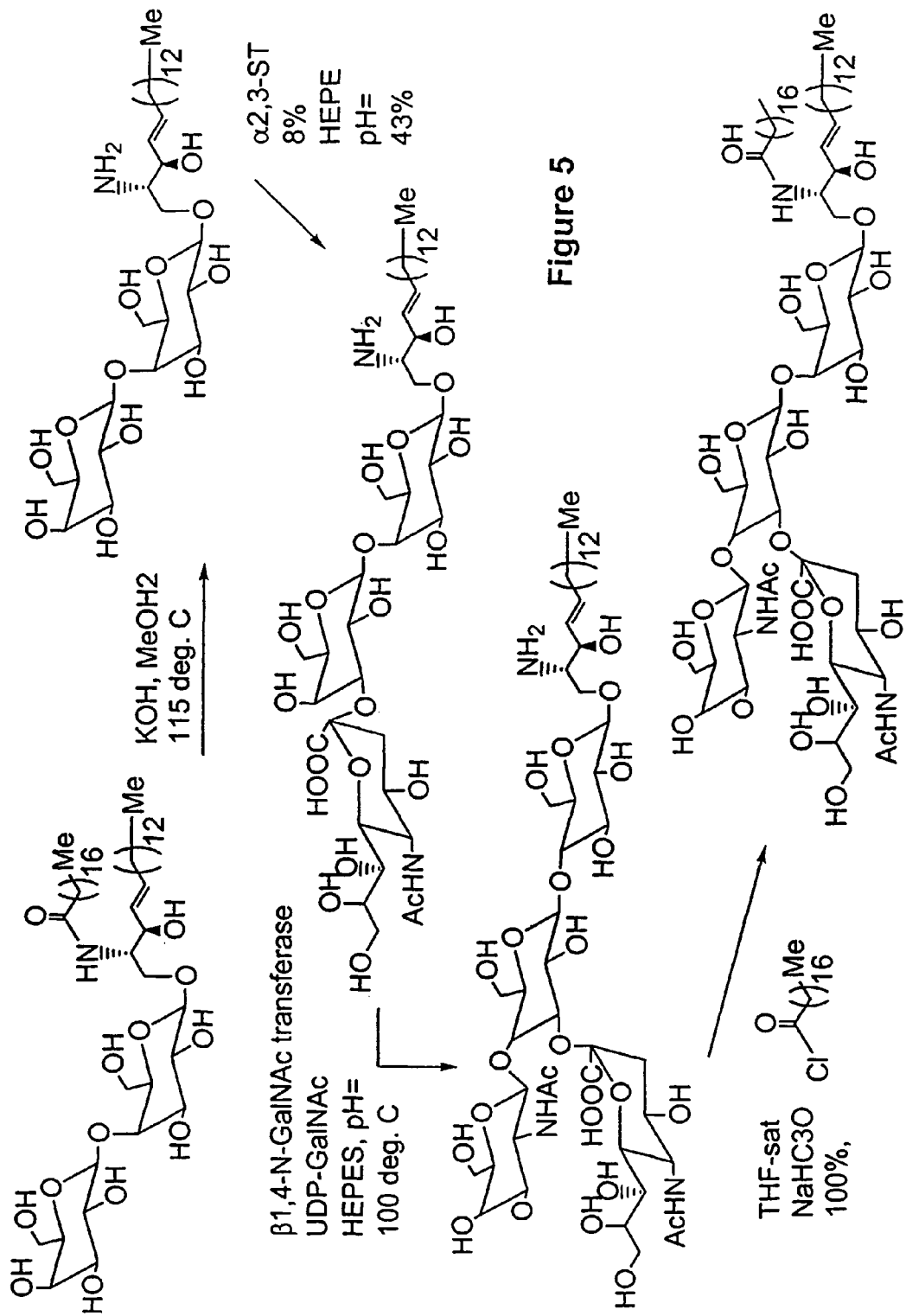
FIG. 5 shows a scheme used for synthesis of the ganglioside GM2 from lactosylceramide via deacylation, two consecutive enzymatic glycosylations, and final chemical acylation.
Figure 6:
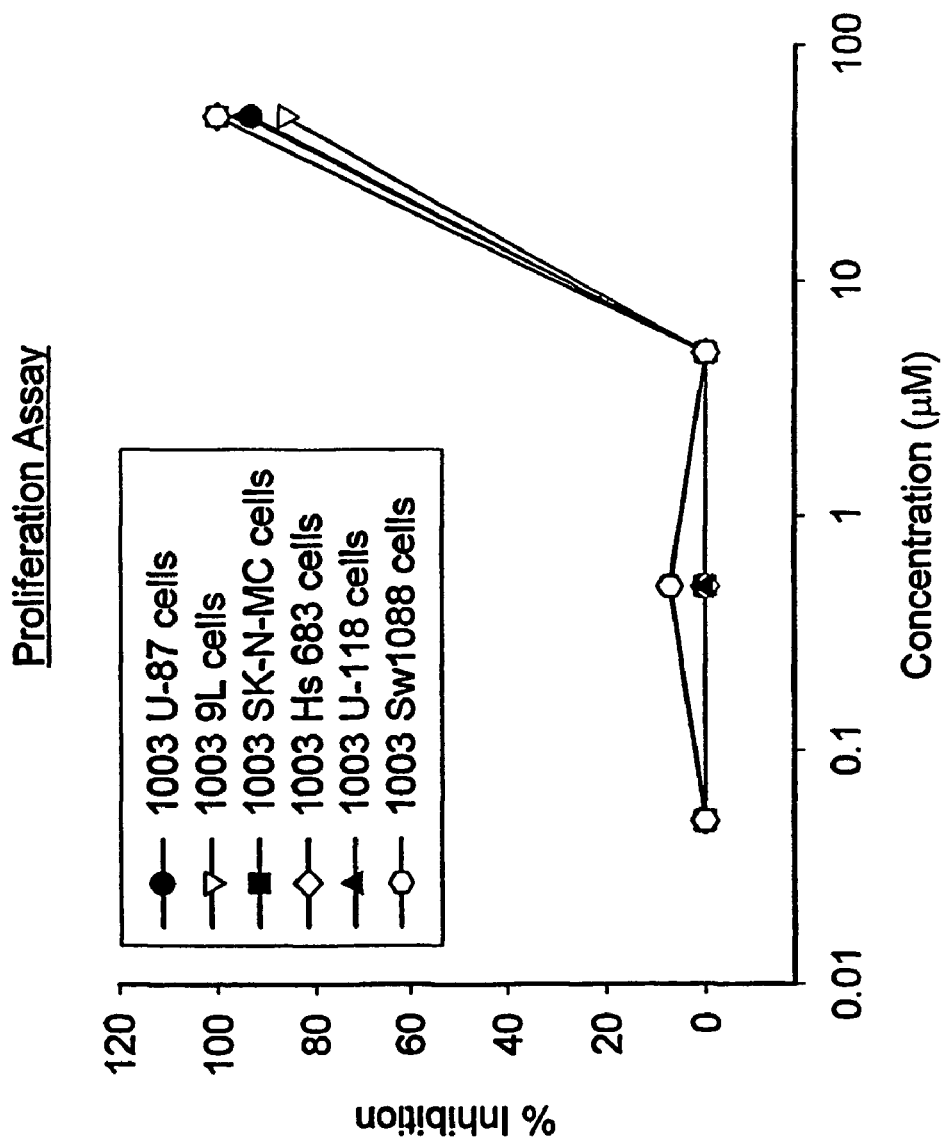
FIGS. 6-15 show attenuation of neuroblastoma cell growth when the neuroblastoma cells are treated with various compounds of the present invention.
Figure 7:
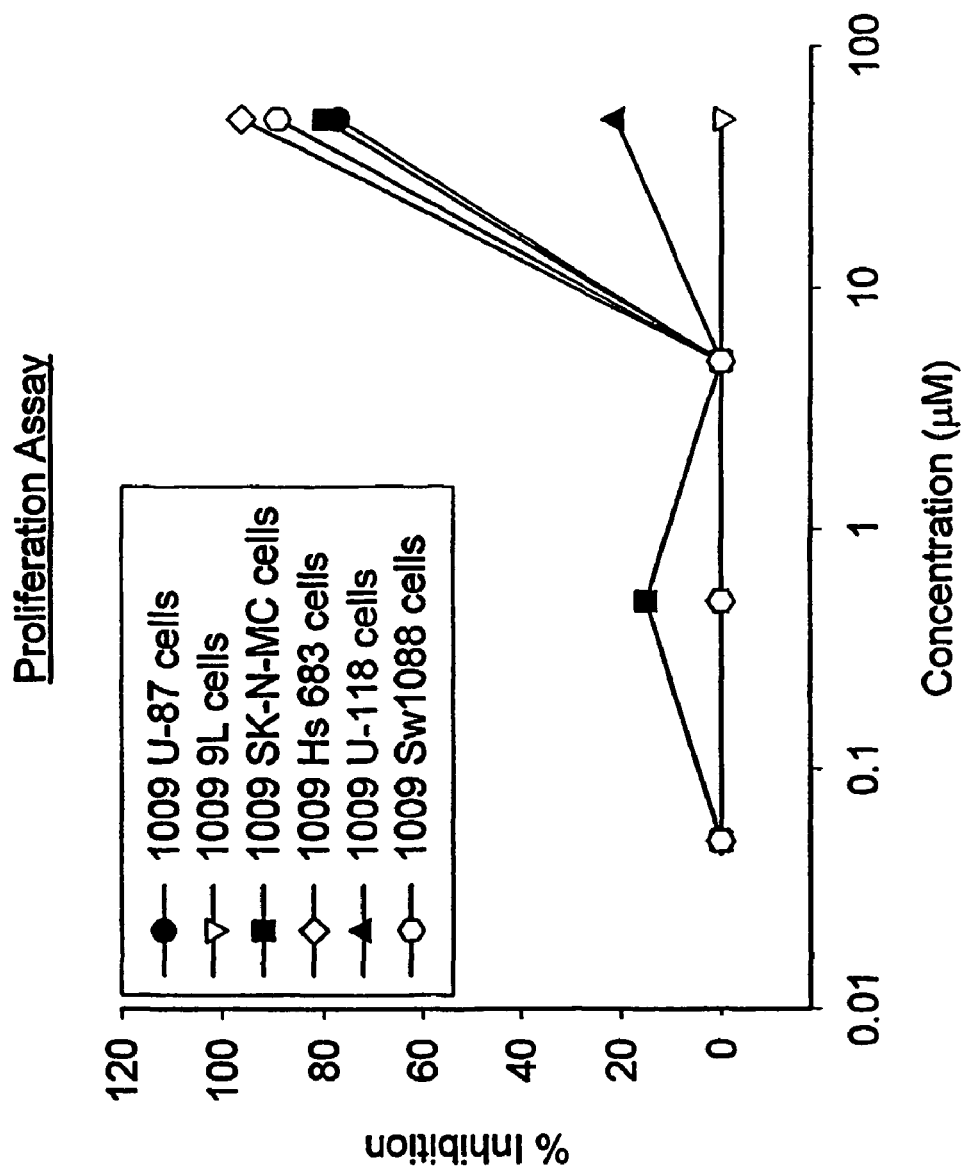
Figure 8:
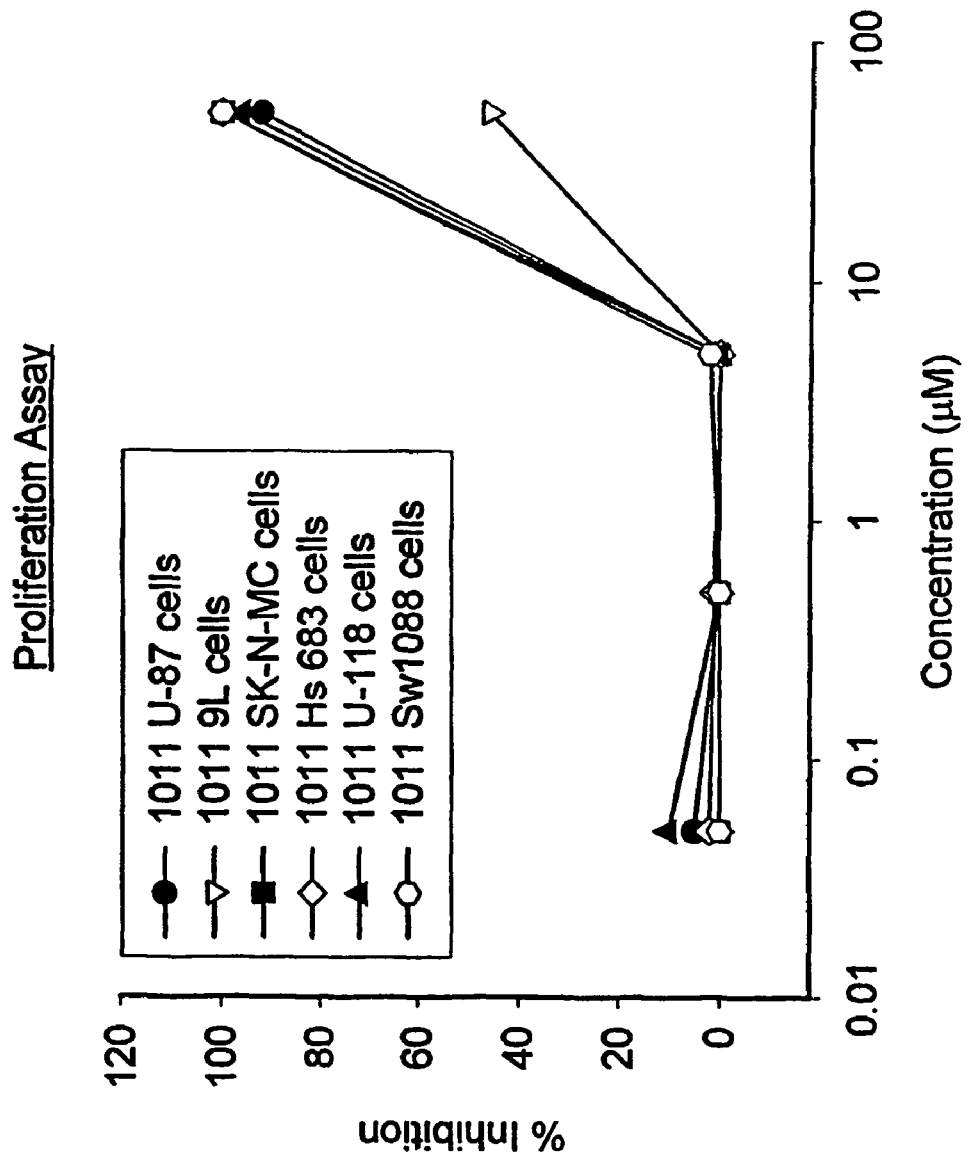
Figure 9:
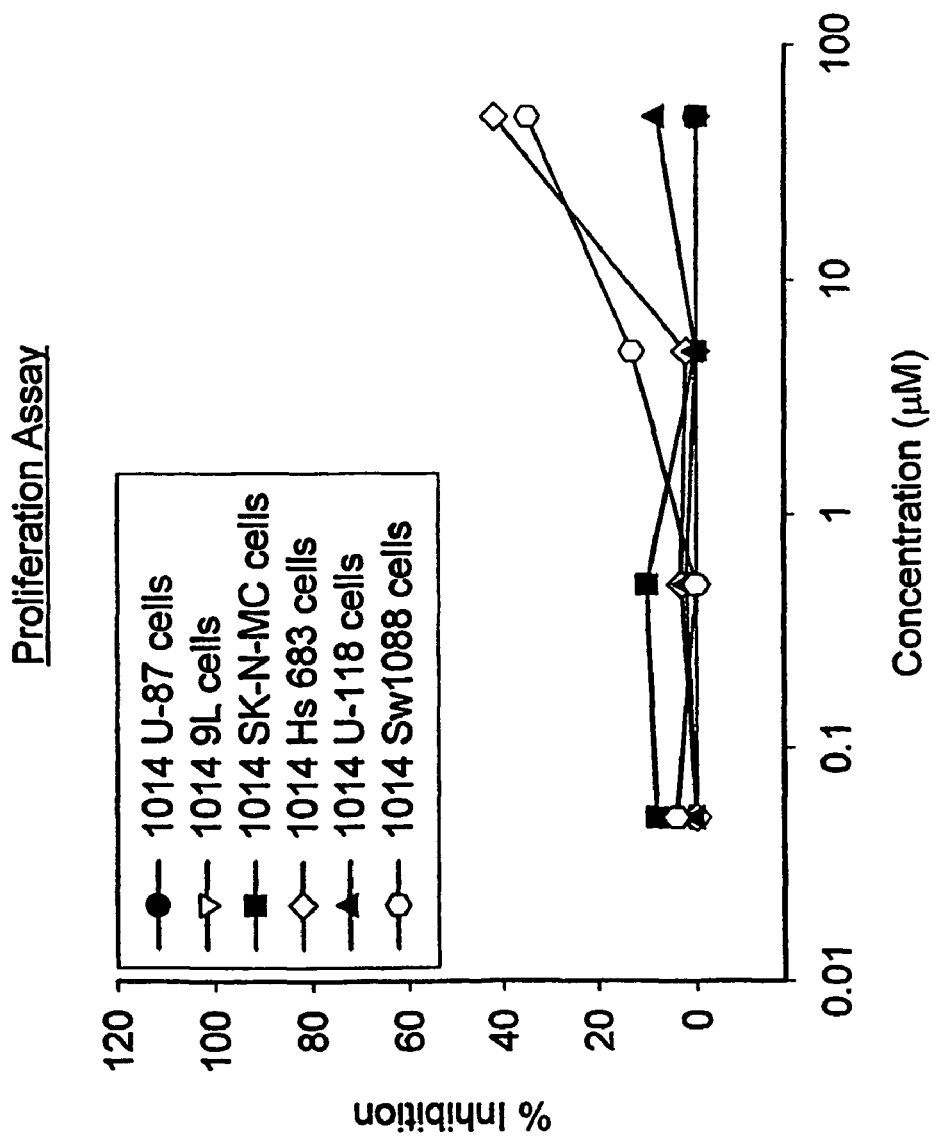
Figure 10:
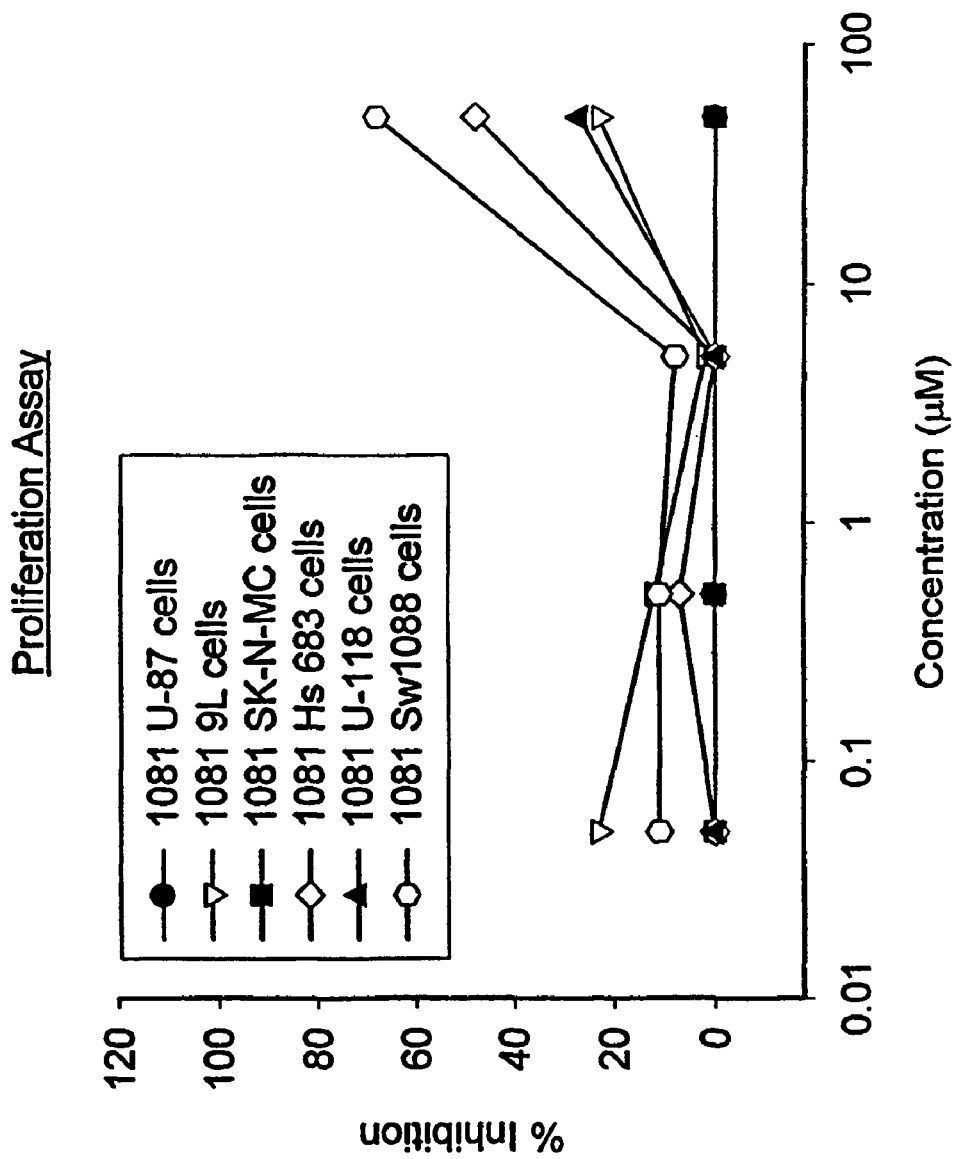
Figure 11:
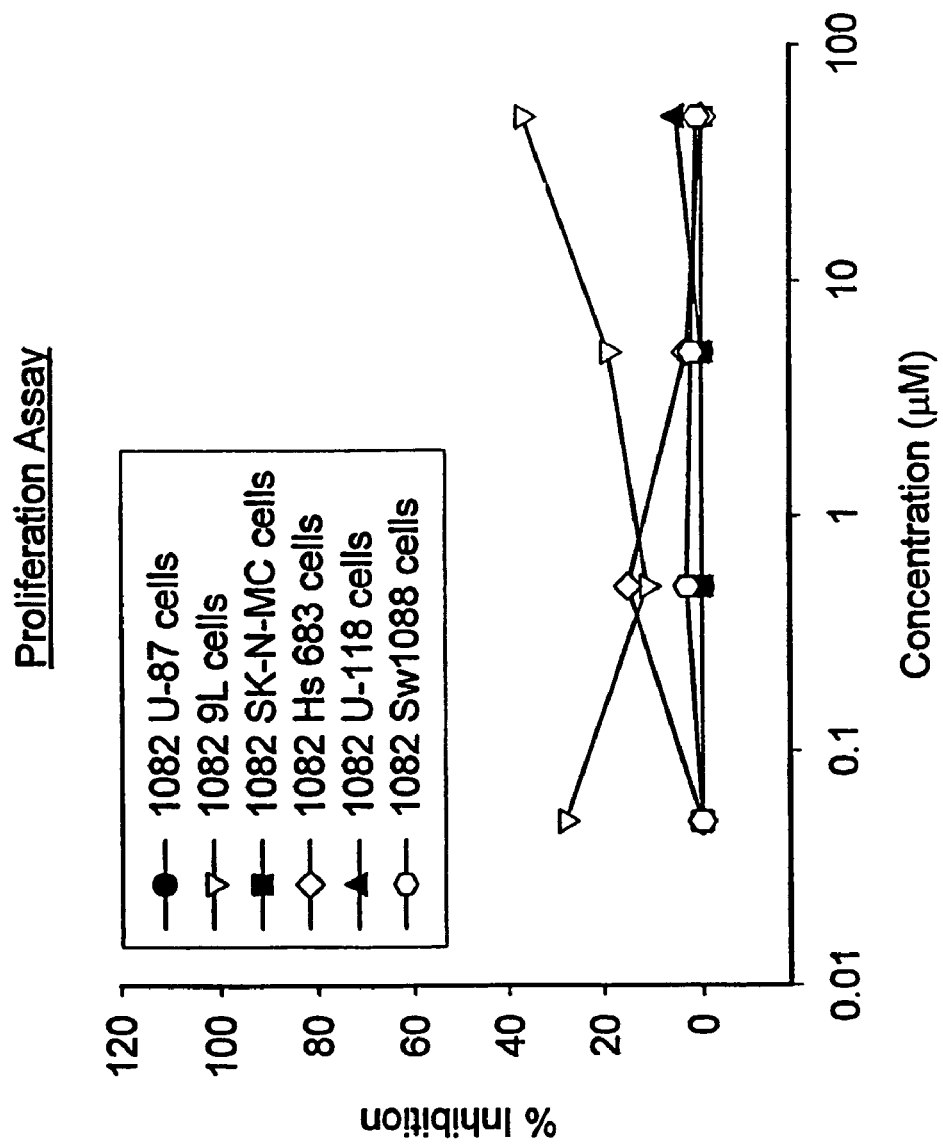
Figure 12:
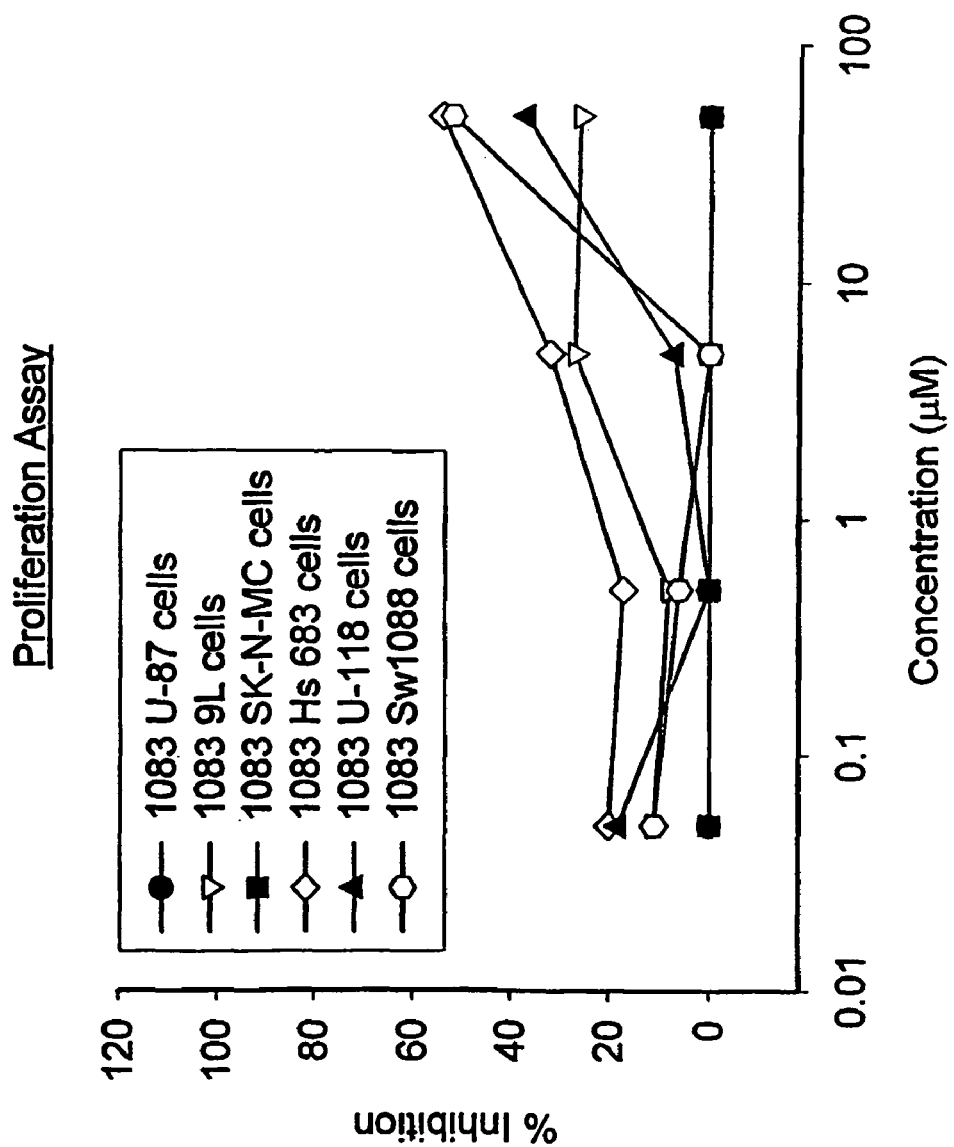
Figure 13:
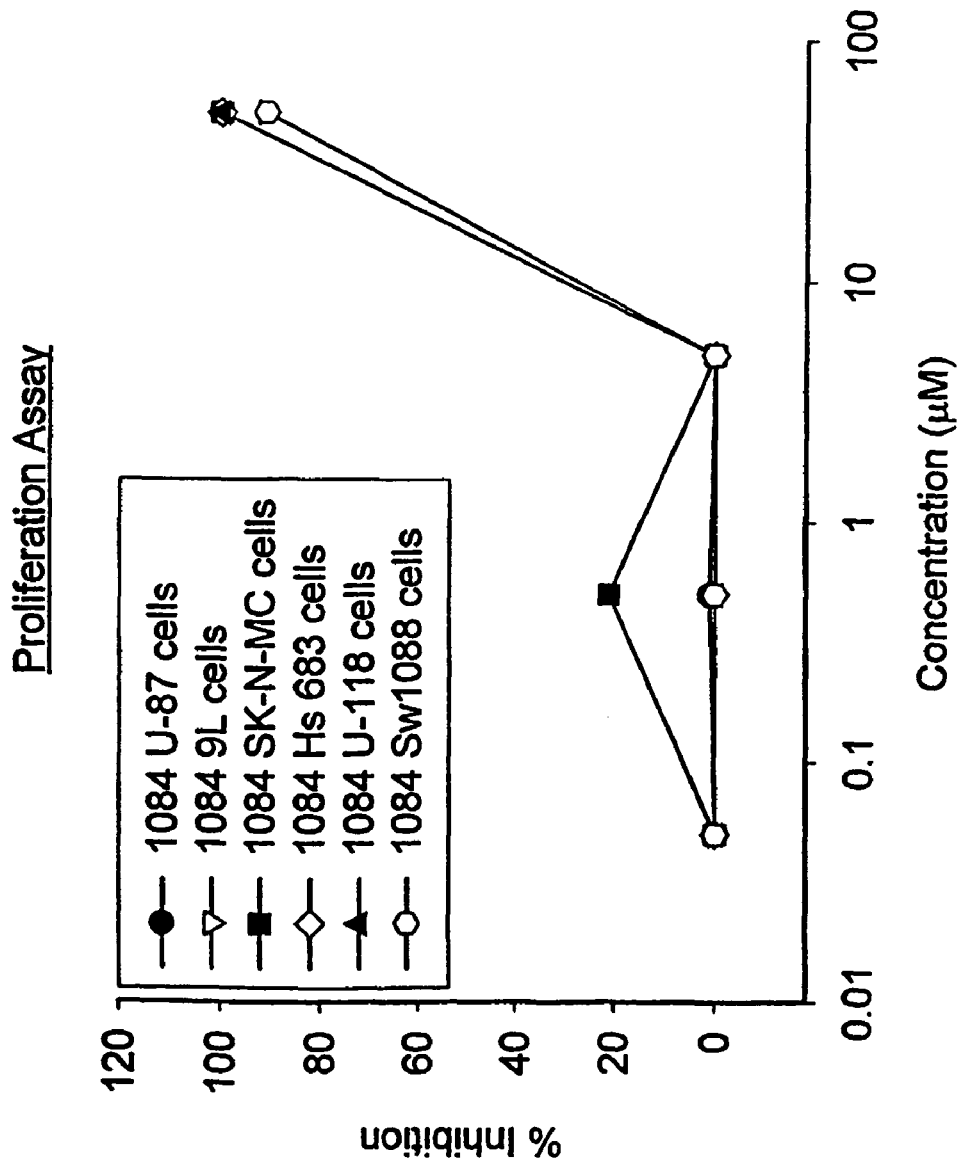
Figure 14:
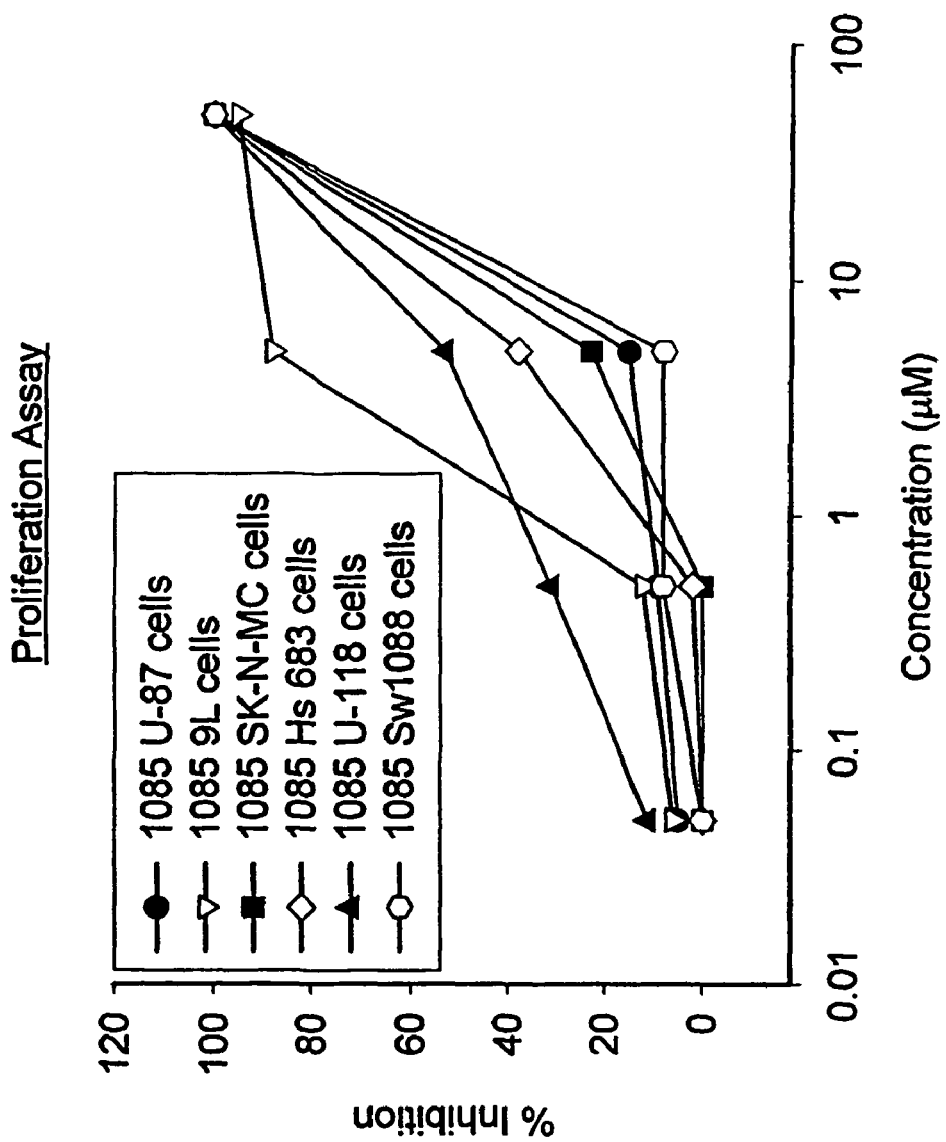
Figure 15:
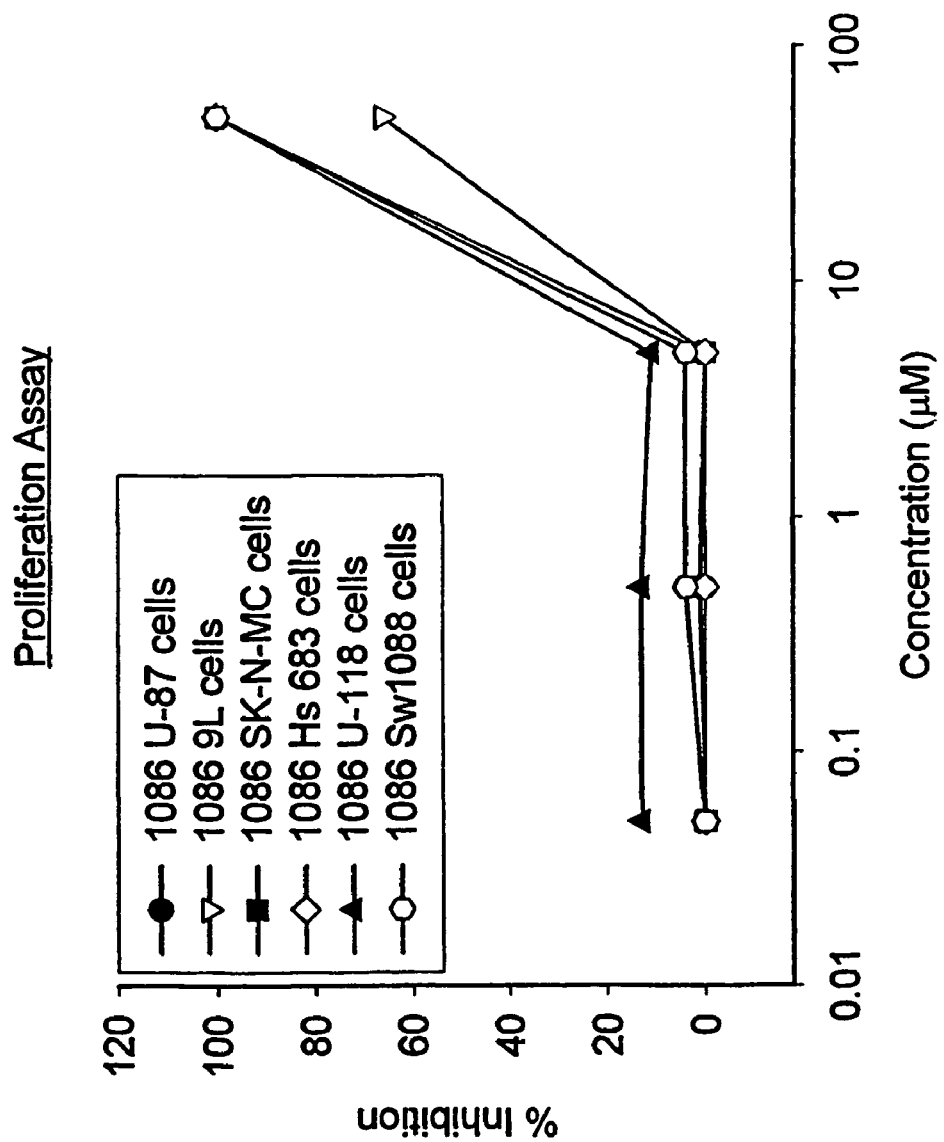

This Example describes three alternative procedures for the synthesis of the $GM_2$ and other gangliosides using a glucosylceramide as the precursor FIG. 4). In Route 1, a β1,4-galactosidase is used to catalyze the transfer of a Gal residue to the glycosylceramide. Simultaneously, an α2,3-sialyltransferase is used in a sialyltransferase cycle to link a sialic acid residue to the Gal. Next, a β1,4-GalNAc transferase is added to the reaction mixture, either with UDP-GalNAc or as part of a GalNAc transferase cycle. In this step, the GalNAc residue is linked to the Gal residue in an α2,3 linkage.

Route 2 differs from the synthesis shown in Route 1 in that the addition of the Gal to the glycosylceramide is catalyzed by a β1,4-galactosyltransferase enzyme, using either a galactosyltransferase cycle or UDP-Glc/Gal as the acceptor sugar. Sialylation and addition of GalNAc are carried out as described above to obtain $GM_2$.

In Route 3, the fatty acid is first removed by treatment with aqueous base prior to the glycosyltransferase steps. The galactosylation, sialylation, and GalNAc transferase reactions are carried out as in Route 2. Following the addition of the GalNAc residue, a fatty acid is linked to the molecule. In the example shown in FIG. 3, an activated $C_{18}$ fatty acid is used, resulting in the synthesis of $GM_2$. Greater efficiency is generally observed when the fatty acid is removed prior to the glycosylation reactions.

After each synthetic route, additional glycosyltransferases can be used to add additional saccharide residues in order to obtain more complex gangliosides.

Example 12

Effect of Compounds of the Invention on Growth of Mammalian Cells

Synthesis of Ganglioside Compounds of the Invention

Compounds 1003, 1009, 1011, 1014, 1081, 1082, 1083, 1084, 1085, and 1086 were made according to methods of the present invention and stored in powder form until use.

Reagents 9L cells were obtained from Wake Forest University (Winston-Salem, N.C.) and the other five cell lines from American Type Culture Collection (ATCC, Manassas, Va.). Minimum essential medium Eagles (MM) and basal medium Eagles (BME) media, fetal bovine serum (FBS), newborn bovine serum, and trypsin-EDTA solution were obtained from Sigma Chemical Co., St. Louis, Mo. Dulbecco's modified Eagle's medium (DMEM) and Liebovitz L-15 medium were obtained from ATCC (Manassas, Va.). MTT dye reagents were obtained from Promega Corporation, Madison, Wis.

Cell Culture 9L cells were grown in BME media with 10% newborn bovine serum, 2 mM glutamine, and 1% penicillin/streptomycin at 37° C. in 5% $CO_2$/95% air. The cell lines obtained from ATCC were grown in the ATCC-recommended medium at 37° C. in 5% $CO_2$/95% air. SK-N-MC (HTB-10) and U-87 (HTB-14) were grown in MEM with Earles salts, 2 mM glutamine, 1 mM pyruvate, 0.1 M non-essential amino acids (NEAA), and 10% FBS. U-118S (HTB-15) and Hs 683 (HTB-138) cells were grown in DMEM, 4 mM glutamine, 4.5 g/L glucose, 1.5 g/L sodium bicarbonate, and 10% FBS. SW 1088 (HTB-12) cells were grown in Liebovitz L-15 medium with 10% FBS in a humidified 37° C. air environment (no added $CO_2$). Medium for each cell line was changed every third day, and cells were passaged weekly using 0.25% trypsin-EDTA solution as the dissociation agent.

Proliferation Assay

Cells at 80% confluence were harvested using 0.25% trypsin-EDTA solution. The trypsinized cells were plated in 96-well plates at 2000 cells per well (with the exception of 9L cells, which were plated at 1200 cells per well as they grow very fast). Working stocks of each of the ten compounds—1003, 1009, 1011, 1014, 1081, 1082, 1083, 1084, 1085, and 1086—were prepared in dimethyl sulfoxide (DMSO). After the cells were allowed to attach for 24 h, the cultures were fed and dosed with each of the ten compounds—1003, 1009, 1011, 1014, 1081, 1082, 1083, 1084, 1085, and 1086—at concentrations of 0.05, 0.5, 5, and 50 µM. For each concentration, replicates of six wells were used. Controls received the same volume of DMSO diluted in medium that was added to the test wells. The culture medium was renewed with fresh test compound every three days. After seven days of culture, the viable cells were measured using MTT reagent. The MTT assay was performed by removing the medium from each well, adding 100 µL of fresh medium and 15 µL of tetrazolium dye solution to each well and incubating the cells at 37° C. for 4 h. After 4 h, 100 µL of solubilization/stop solution was added to each well. The plates were incubated at room temperature overnight, and the intensity of the yellow color of each well was measured at 575 nm on a Bio-Tek Instruments (Winooski, Vt.) microplate scanning spectrophotometer.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated in their entirety by reference.

What is claimed is:

1. A synthetic compound having a formula selected from the group consisting of (Va), (Vb), (Vc) and (Vd):

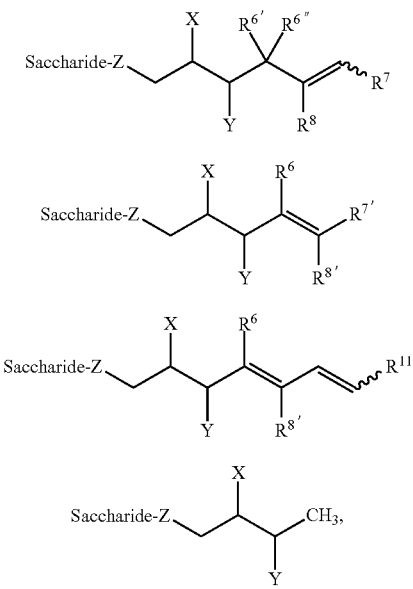

wherein the saccharide portion is selected from the group consisting of

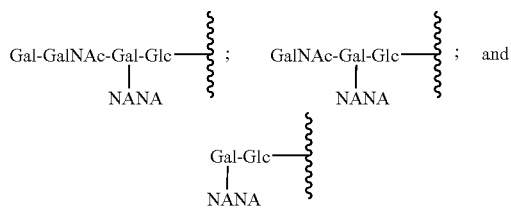

X is $NR^1R^2$;
Y is —OH;
Z is O;

each $R^1$ and $R^2$ are independently selected from the group consisting of —C(=M)$R^3$, and —C(=M)-p-$R^3$;
wherein M and p are independently selected from O, $NR^4$ and S;
$R^3$ is H, alkyl, arylalkyl, haloalkyl, aryl, heteroaryl, or heteroalkyl;
$R^4$ is H, alkyl, aryl, arylalkyl, heteroaryl, heteroalkyl, or haloalkyl;
$R^6$ is H;
$R^{6'}$ is —$NR^9R^{10}$;
$R^{6''}$ is H;
$R^7$ and $R^8$ are independently H, and aryl, where, $R^7$ and $R^8$ are optionally substituted with at least one group selected from the group consisting of halo, haloalkyl, alkoxy, and thiohaloalkyl;
$R^{7'}$ and $R^{8'}$ are independently H, alkenyl, —C(=O)$NR^9R^{10}$, aryl, heteroaryl, or a linked bicyclic mixture of aryl and heteroaryl, where $R^{7'}$ and $R^{8'}$ are optionally substituted with at least one group selected from the group consisting of halo, haloalkyl, alkoxy, and thiohaloalkyl;
$R^9$, $R^{10}$, and $R^{11}$ are independently alkyl, cycloalkyl, aryl, arylalkyl, heteroaryl, or heteroalkyl, where $R^9$, $R^{10}$, and $R^{11}$ are optionally substituted, preferably-substituted with at least one group selected from the group consisting of halo, haloalkyl, alkoxy, and thiohaloalkyl; or where $R^9$ and $R^{10}$ taken together with the nitrogen to which they are attached form a heterocyclic ring comprising at least one heteroatom selected from N, O and S;
and all pharmaceutically acceptable salts, and geometric isomers thereof.

2. A compound of claim 1, wherein the saccharide portion is

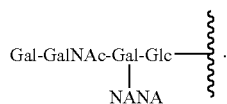

3. A synthetic compound selected from the group consisting of:

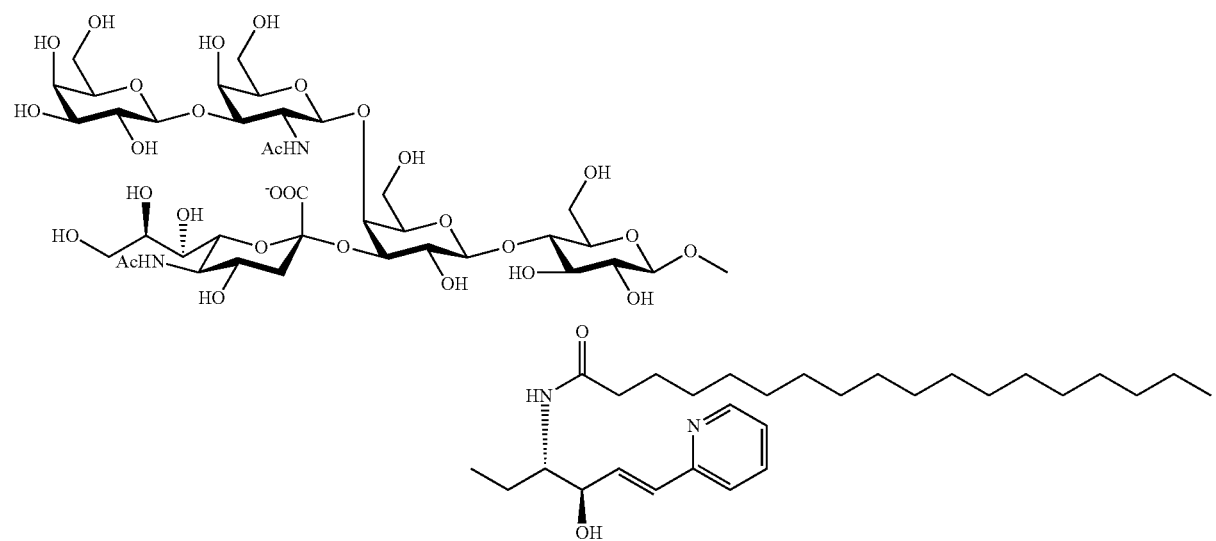

-continued
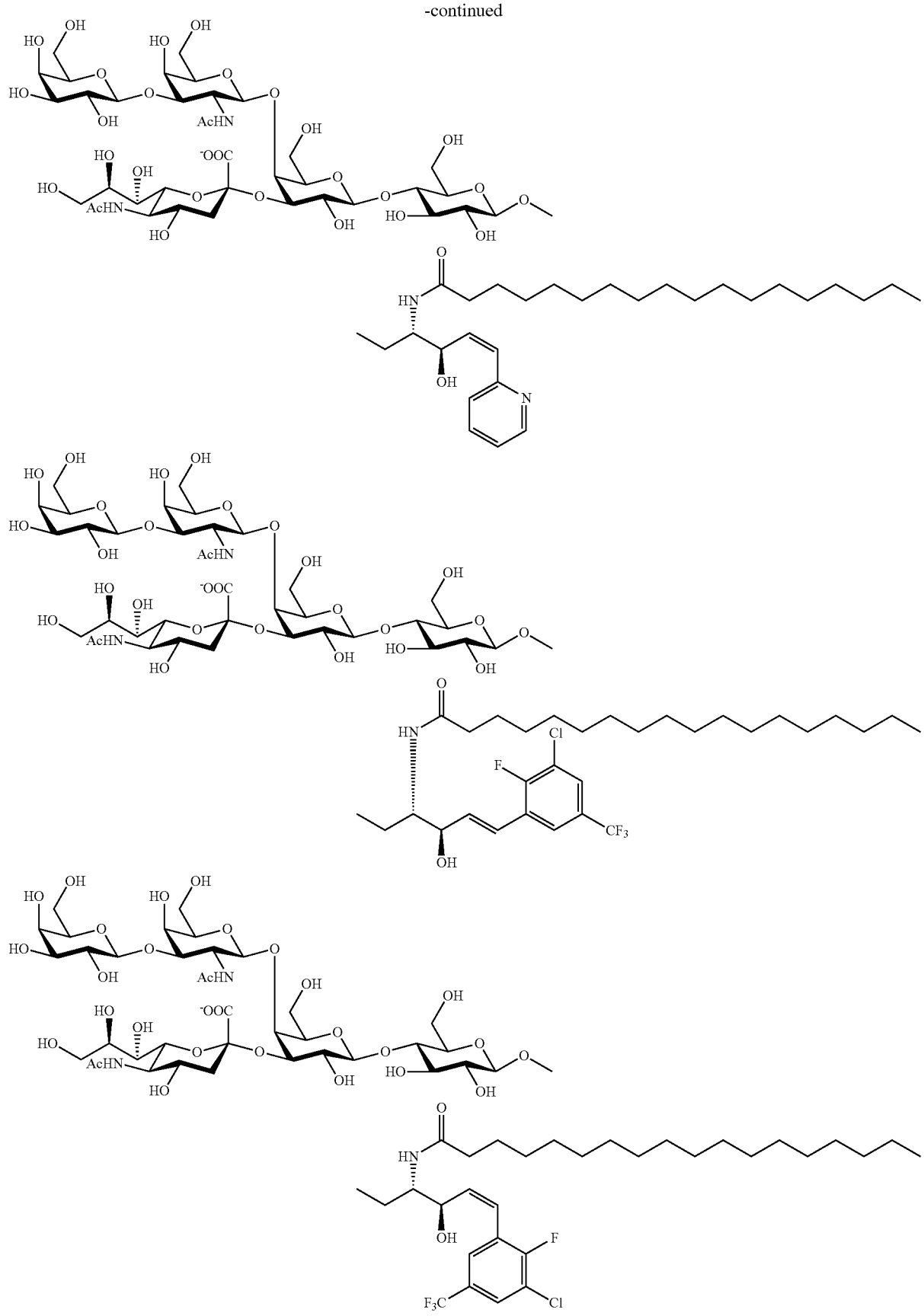

-continued
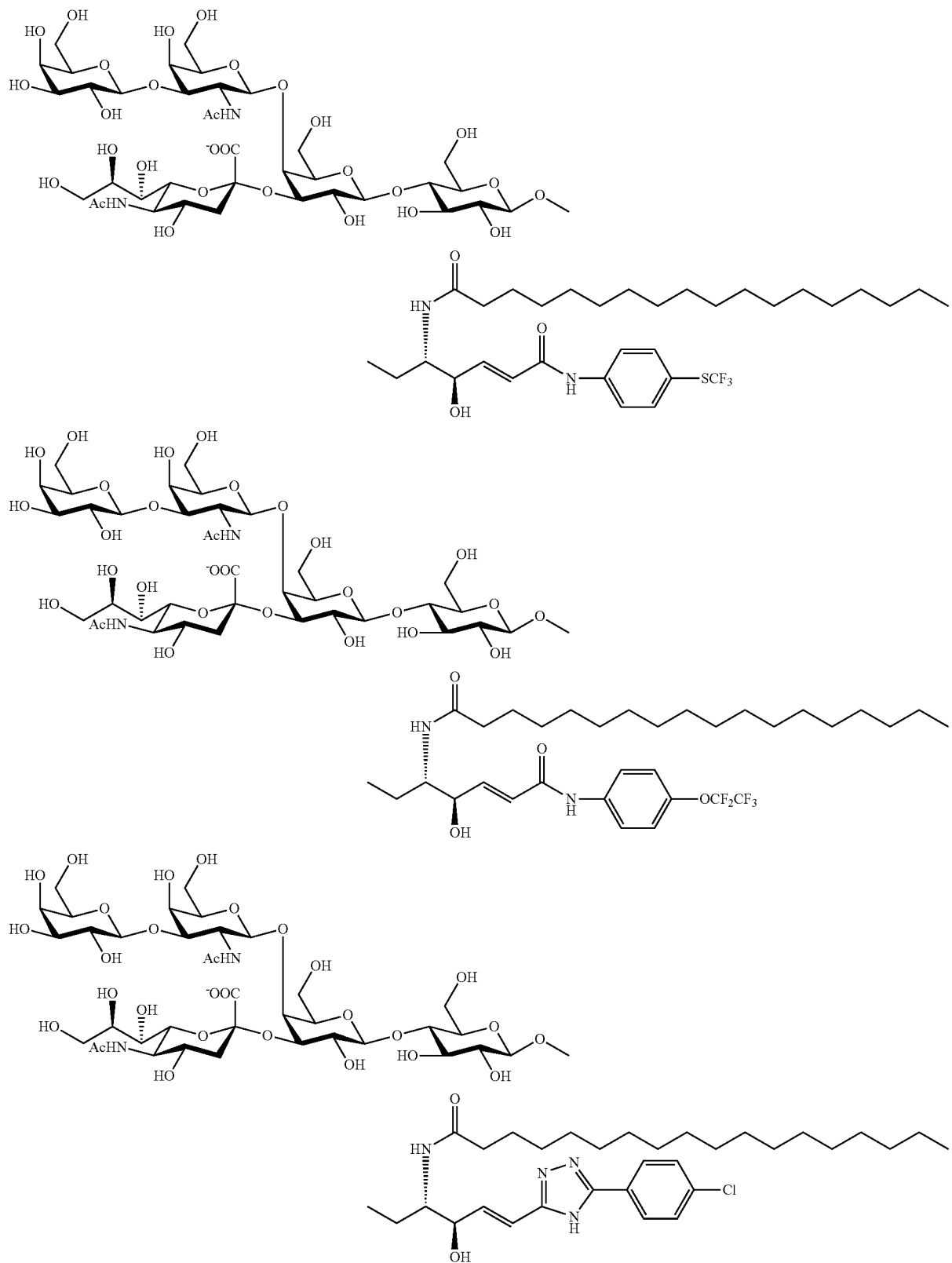

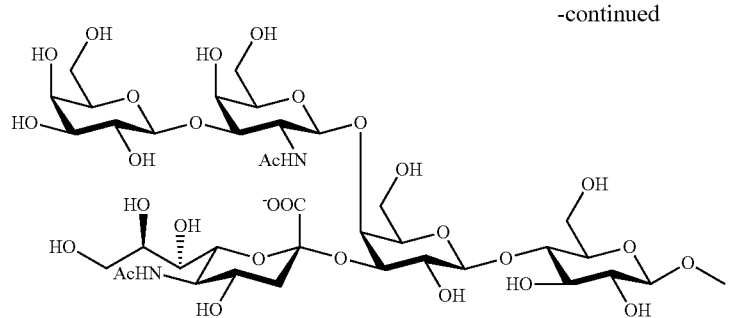
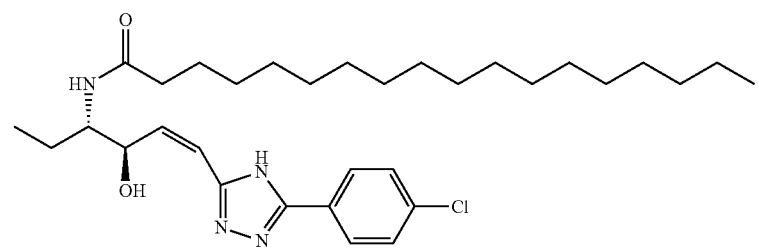
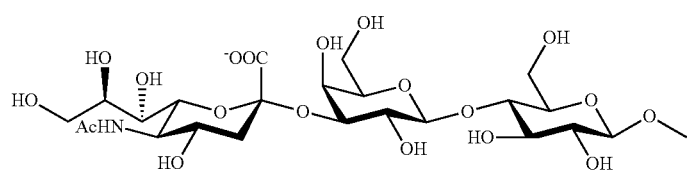
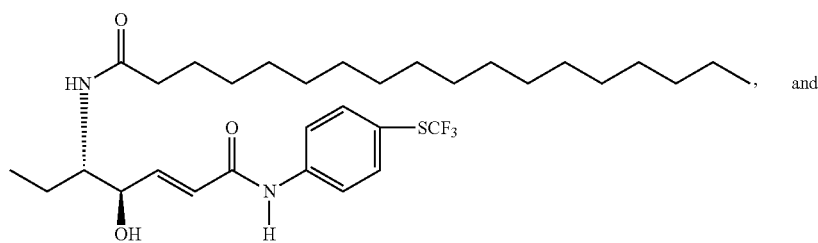
, and
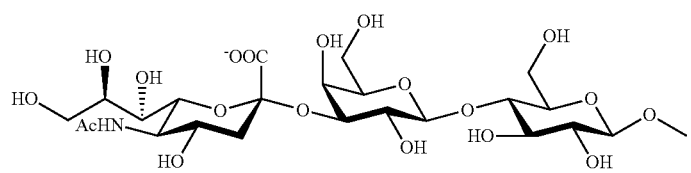
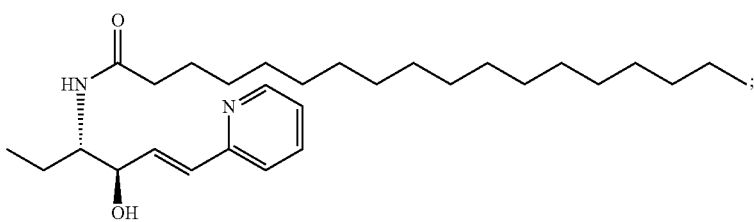
and all pharmaceutically acceptable salts, and geometric isomers thereof.

4. A synthetic compound having a formula selected from the group consisting of:
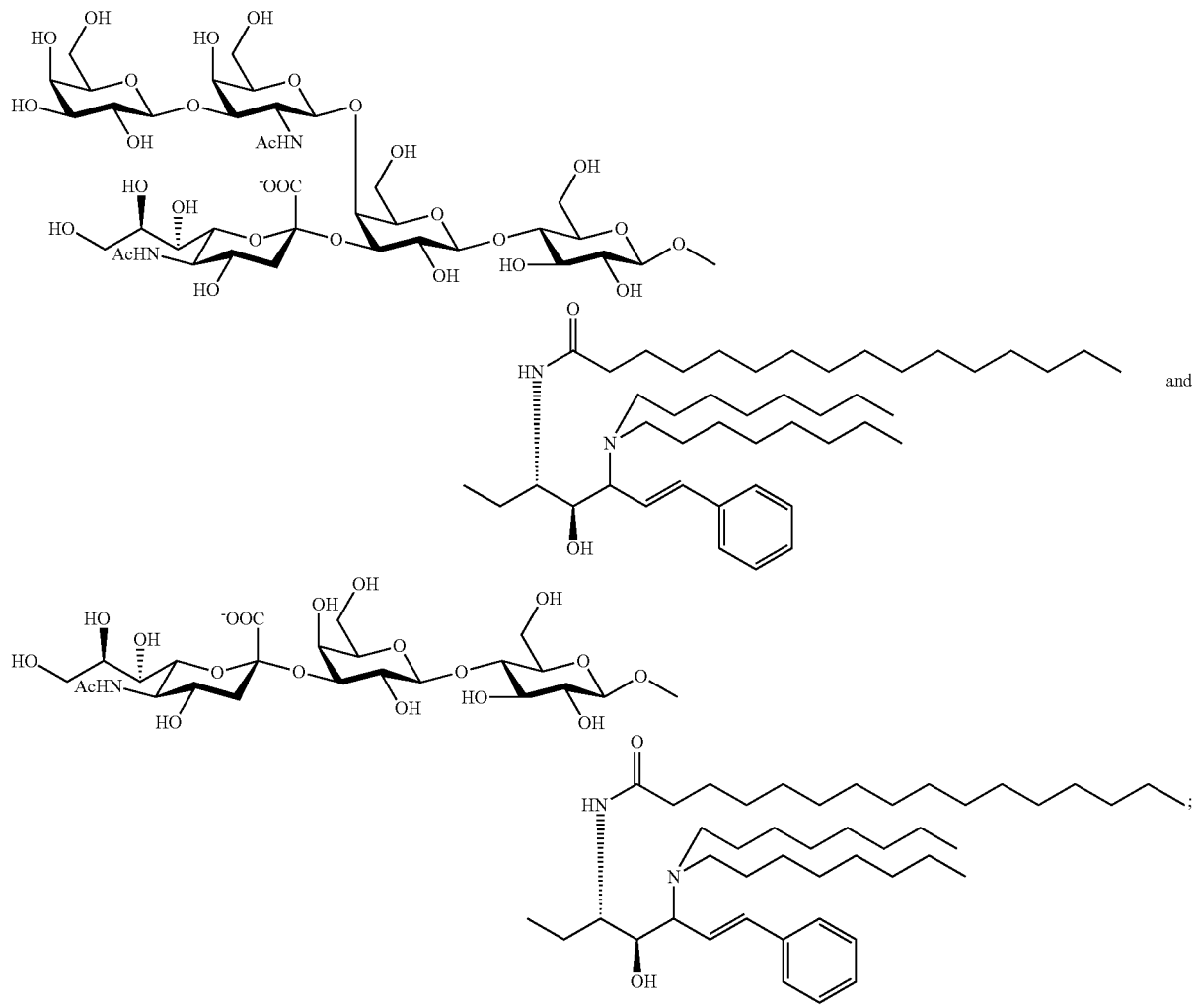
and all pharmaceutically acceptable salts, and geometric isomers thereof.
5. A synthetic compound having the formula:
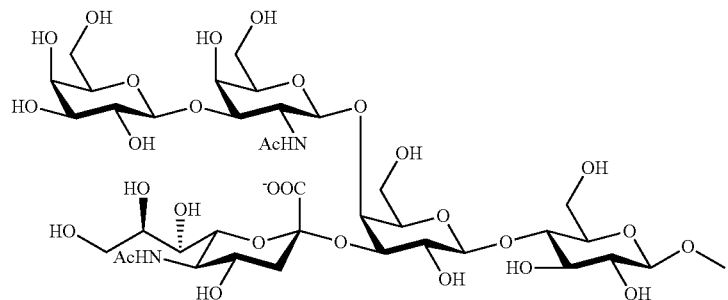

-continued

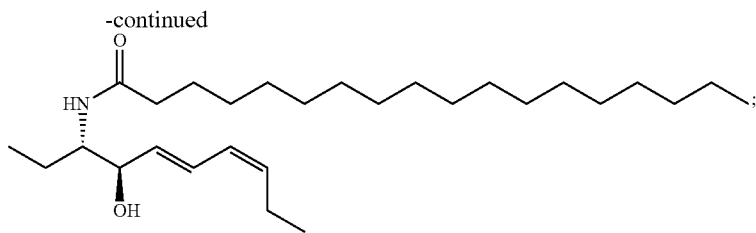

and all pharmaceutically acceptable salts, and geometric isomers thereof.

6. A pharmaceutical composition comprising the compound according to claim 1 and a pharmaceutically acceptable carrier.

7. A pharmaceutical composition comprising the compound according to claim 3 and a pharmaceutically acceptable carrier.

8. A pharmaceutical composition comprising the compound according to claim 4 and a pharmaceutically acceptable carrier.

9. A pharmaceutical composition comprising the compound according to claim 5 and a pharmaceutically acceptable carrier.

* * * * *